(12) United States Patent
Vayser et al.

(10) Patent No.: US 9,510,737 B2
(45) Date of Patent: *Dec. 6, 2016

(54) ILLUMINATED SUCTION APPARATUS

(71) Applicant: Invuity, Inc., San Francisco, CA (US)

(72) Inventors: Alex Vayser, Mission Viejo, CA (US); Fernando Erismann, New York, NY (US); Douglas Rimer, Los Altos Hills, CA (US); Vladimir Zagatsky, San Francisco, CA (US)

(73) Assignee: Invuity, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/061,990

(22) Filed: Mar. 4, 2016

(65) Prior Publication Data

US 2016/0213233 A1 Jul. 28, 2016

Related U.S. Application Data

(63) Continuation of application No. 14/732,617, filed on Jun. 5, 2015, now Pat. No. 9,308,054, which is a continuation of application No. 14/057,947, filed on Oct. 18, 2013, now Pat. No. 9,072,452, which is a continuation of application No. 13/712,029, filed on Dec. 12, 2012, now Pat. No. 8,795,162, which is a
(Continued)

(51) Int. Cl.
| | |
|---|---|
| *A61B 1/06* | (2006.01) |
| *A61B 1/015* | (2006.01) |
| *A61B 1/07* | (2006.01) |
| *A61M 1/00* | (2006.01) |

(52) U.S. Cl.
CPC ............... *A61B 1/015* (2013.01); *A61B 1/06* (2013.01); *A61B 1/07* (2013.01); *A61M 1/008* (2013.01)

(58) Field of Classification Search
CPC ..... A61B 1/06; A61B 1/0607; A61B 1/00135; A61B 1/0017; A61B 1/015; A61B 1/07; A61B 1/0039; A61B 1/008; A61B 1/0023; A61B 1/0031; A61M 1/008
USPC ............... 600/101, 104, 121, 123, 125, 130, 139,600/140, 153, 154, 156, 160, 178, 179, 182,600/184, 187, 188, 191, 199, 249

See application file for complete search history.

(56) References Cited

U.S. PATENT DOCUMENTS

| | | |
|---|---|---|
| 510,524 A | 12/1893 | Smith |
| 3,261,356 A | 7/1966 | Wallace |

(Continued)

FOREIGN PATENT DOCUMENTS

| | | |
|---|---|---|
| CN | 101209214 A | 4/2011 |
| EP | 0101781 A1 | 3/1984 |

(Continued)

OTHER PUBLICATIONS

European search report and opinion dated Nov. 5, 2013 for EP Application No. 11848284.3.
(Continued)

*Primary Examiner* — Pedro Philogene
*Assistant Examiner* — David C Comstock
(74) *Attorney, Agent, or Firm* — Wilson Sonsini Goodrich & Rosati

(57) ABSTRACT

An illuminated suction apparatus including a hand-held surgical device combining a high-performance non-fiber optic optical waveguide with suction. This device is useful in a wide array of surgical procedures including open and minimally invasive orthopedics.

26 Claims, 32 Drawing Sheets

Related U.S. Application Data continuation-in-part of application No. 13/328,773, filed on Dec. 16, 2011, now Pat. No. 8,568,304, said application No. 13/712,029 is a continuation-in-part of application No. 13/619,574, filed on Sep. 14, 2012, which is a continuation of application No. 12/616,095, filed on Nov. 10, 2009, now Pat. No. 8,292,805.

(60) Provisional application No. 61/423,813, filed on Dec. 16, 2010.

(56) References Cited

U.S. PATENT DOCUMENTS

| | | | |
|---|---|---|---|
| 3,626,471 A * | 12/1971 | Florin | A61M 1/0084 600/205 |
| 3,638,644 A | 2/1972 | Franklin | |
| 3,641,332 A * | 2/1972 | Reick | A61B 1/07 264/1.24 |
| 3,890,960 A | 6/1975 | Wunsch et al. | |
| 4,226,228 A | 10/1980 | Shin et al. | |
| 4,562,832 A * | 1/1986 | Wilder | A61B 1/32 138/DIG. 8 |
| 4,592,344 A | 6/1986 | Scheer | |
| 4,597,030 A | 6/1986 | Brody et al. | |
| 4,605,990 A | 8/1986 | Wilder et al. | |
| 4,643,172 A | 2/1987 | Taff et al. | |
| 4,697,578 A | 10/1987 | Burgin | |
| 4,733,332 A | 3/1988 | Yamashita et al. | |
| 4,807,599 A | 2/1989 | Robinson et al. | |
| 4,842,356 A | 6/1989 | Mori | |
| 4,872,837 A | 10/1989 | Issalene et al. | |
| 4,961,617 A | 10/1990 | Shahidi et al. | |
| 4,992,047 A | 2/1991 | Warner | |
| 5,035,232 A | 7/1991 | Lutze et al. | |
| 5,085,657 A | 2/1992 | Ben-Simhon | |
| 5,213,092 A | 5/1993 | Uram | |
| 5,290,279 A * | 3/1994 | Bonati | A61B 1/317 600/108 |
| 5,324,285 A | 6/1994 | Cannon | |
| 5,353,786 A | 10/1994 | Wilk | |
| 5,588,952 A | 12/1996 | Dandolu | |
| 5,651,783 A | 7/1997 | Reynard | |
| 5,882,194 A * | 3/1999 | Davis | A61C 17/043 433/29 |
| 5,931,670 A | 8/1999 | Davis | |
| 6,185,356 B1 | 2/2001 | Parker et al. | |
| 6,504,985 B2 | 1/2003 | Parker et al. | |
| 7,248,772 B2 | 7/2007 | Suzuki et al. | |
| 7,306,559 B2 | 12/2007 | Williams | |
| 7,620,279 B2 | 11/2009 | Joseph et al. | |
| 7,842,027 B2 | 11/2010 | Lieponis | |
| 7,901,353 B2 | 3/2011 | Vayser et al. | |
| 8,292,805 B2 * | 10/2012 | Vayser | A61B 1/0017 600/249 |
| 8,568,304 B2 * | 10/2013 | Vayser | A61B 1/00135 600/184 |
| 8,795,162 B2 * | 8/2014 | Vayser | A61B 1/00135 600/184 |
| 8,870,761 B2 | 10/2014 | Vayser et al. | |
| 8,936,551 B2 | 1/2015 | Vayser et al. | |
| 9,044,161 B2 | 6/2015 | Vayser et al. | |
| 9,072,452 B2 * | 7/2015 | Vayser | A61B 1/00135 |
| 9,308,054 B2 * | 4/2016 | Vayser | A61B 1/015 |
| 2002/0002366 A1 | 1/2002 | Grasso et al. | |
| 2003/0095781 A1 | 5/2003 | Williams | |
| 2006/0211918 A1 | 9/2006 | Lieponis | |
| 2008/0045799 A1 | 2/2008 | Whitehead et al. | |
| 2008/0089088 A1 * | 4/2008 | Joseph | A61C 17/043 362/573 |
| 2008/0266840 A1 * | 10/2008 | Nordmeyer | A61B 90/36 362/119 |
| 2008/0269735 A1 | 10/2008 | Vila et al. | |
| 2008/0275298 A1 | 11/2008 | Ratnakar | |
| 2009/0221991 A1 | 9/2009 | Lieponis | |
| 2010/0190129 A1 | 7/2010 | Paz | |
| 2011/0112376 A1 | 5/2011 | Vayser et al. | |
| 2012/0184946 A1 | 7/2012 | Price et al. | |
| 2013/0012783 A1 | 1/2013 | Vayser et al. | |
| 2014/0005490 A1 | 1/2014 | Vayser et al. | |
| 2014/0024901 A1 | 1/2014 | Vayser et al. | |
| 2014/0088371 A1 | 3/2014 | Vayser et al. | |

FOREIGN PATENT DOCUMENTS

| | | |
|---|---|---|
| EP | 2498837 A2 | 9/2012 |
| GB | 2078526 A | 1/1982 |
| JP | S5924805 A | 2/1984 |
| JP | H03139344 A | 9/1991 |
| JP | 2002515774 A | 5/2002 |
| JP | 2003162904 A | 6/2003 |
| JP | 2008534237 A | 8/2008 |
| WO | WO-2004108188 A1 | 12/2004 |
| WO | WO-2009069837 A1 | 6/2009 |
| WO | WO-2009116969 A1 | 9/2009 |
| WO | WO-2011059985 A2 | 5/2011 |
| WO | WO-2012083247 A1 | 6/2012 |

OTHER PUBLICATIONS

International search report and written opinion dated Apr. 23, 2014 for PCT Application No. US13/74748.
International search report and written opinion dated May 8, 2012 for PCT Application No. US2011/65636.
Notice of allowance dated Dec. 10, 2015 for U.S. Appl. No. 14/732,617.
Notice of allowance dated Jan. 28, 2015 for U.S. Appl. No. 14/308,252.
Notice of allowance dated Feb. 9, 2016 for U.S. Appl. No. 14/732,617.
Notice of allowance dated Mar. 18, 2015 for U.S. Appl. No. 14/057,947.
Notice of allowance dated Mar. 27, 2014 for U.S. Appl. No. 13/712,029.
Notice of allowance dated Apr. 30, 2015 for U.S. Appl. No. 14/057,947.
Notice of allowance dated Jun. 24, 2014 for U.S. Appl. No. 13/712,020.
Notice of allowance dated Jun. 27, 2013 for U.S. Appl. No. 13/328,773.
Notice of allowance dated Aug. 21, 2014 for U.S. Appl. No. 14/039,823.
Notice of allowance dated Dec. 18, 2014 for U.S. Appl. No. 14/039,823.
Office action dated Apr. 11, 2014 for U.S. Appl. No. 14/039,823.
Office action dated Jul. 13, 2015 for U.S. Appl. No. 14/732,617.
Office action dated Aug. 15, 2014 for U.S. Appl. No. 14/308,252.
Office action dated Nov. 21, 2014 for U.S. Appl. No. 14/057,947.
Office action dated Dec. 24, 2013 for U.S. Appl. No. 13/712,020.

* cited by examiner

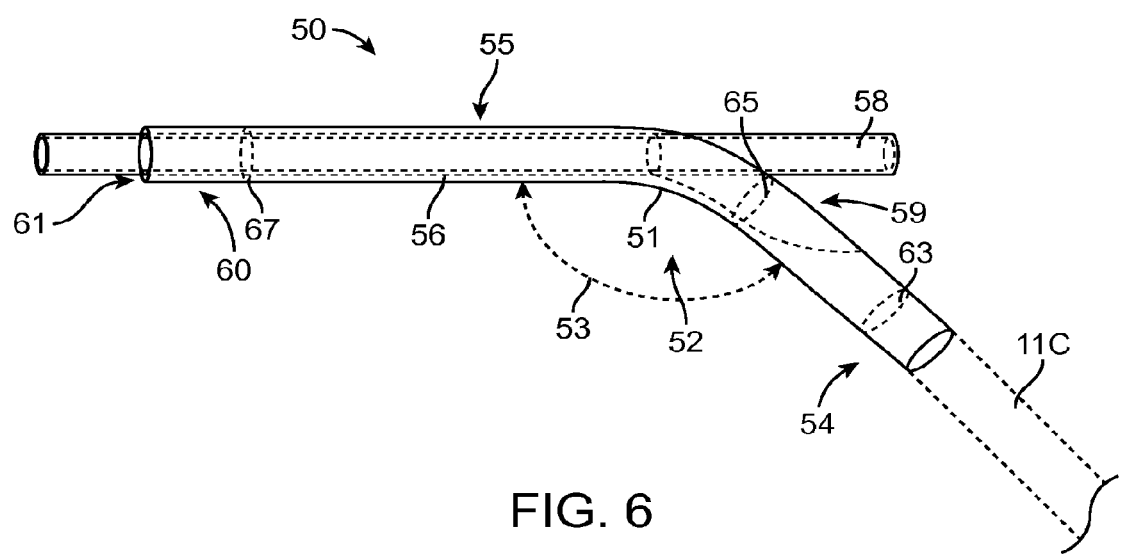
FIG. 6
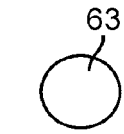
FIG. 6A
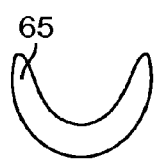
FIG. 6B
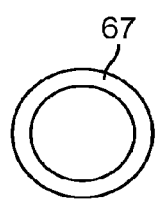
FIG. 6C
FIG. 6D

VIEW C-C

VIEW D-D

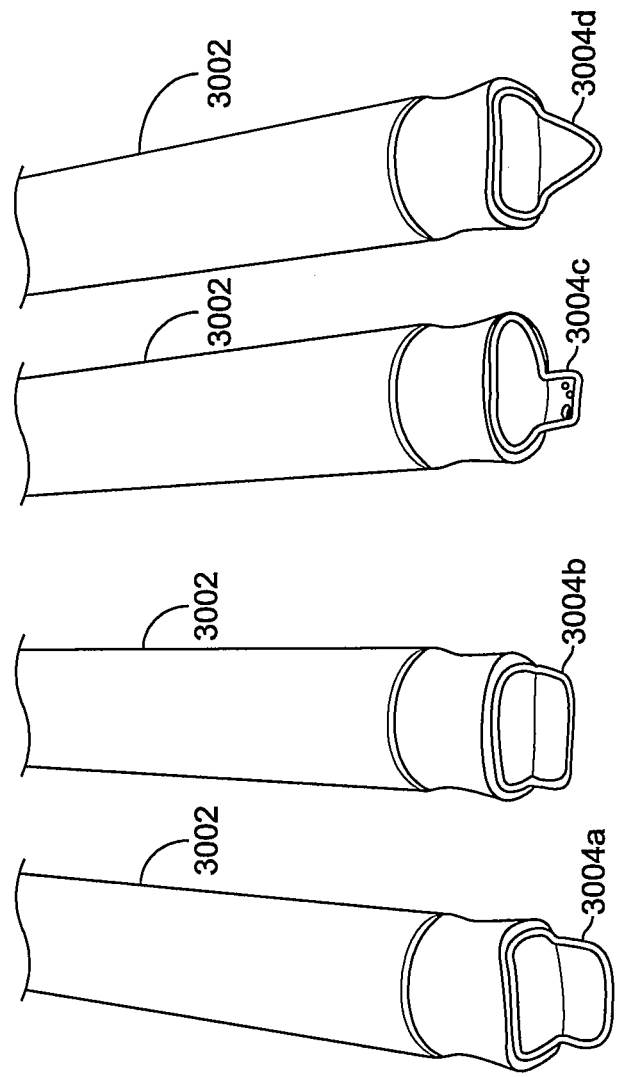

ILLUMINATED SUCTION APPARATUS

CROSS-REFERENCE

The present application is a continuation of U.S. patent application Ser. No. 14/732,617, filed Jun. 5, 2015, which is a continuation of U.S. patent application Ser. No. 14/057,947, now U.S. Pat. No. 9,072,452), filed Oct. 18, 2013, which is a continuation of U.S. patent application Ser. No. 13/712,029, now U.S. Pat. No. 8,795,162), filed Dec. 12, 2012, which is a continuation in part of U.S. patent application Ser. No. 13/328,773, now U.S. Pat. No. 8,568,304) filed Dec. 16, 2011, which is a non-provisional of, and claims the benefit of U.S. Provisional Patent Application No. 61/423,813, formerly 028638-001600US) filed Dec. 16, 2010; U.S. patent application Ser. No. 13/712,029, filed Dec. 12, 2012, is also a continuation in part of U.S. patent application Ser. No. 13/619,574, which is a continuation of U.S. patent application Ser. No. 12/616,095, now U.S. Pat. No. 8,292,805) filed Nov. 10, 2009; the entire contents of which are incorporated herein by reference.

BACKGROUND OF THE INVENTION

In various surgical procedures, illumination of the surgical field is typically achieved through the use of headlamps and surgical microscopes. There are scenarios in which these illumination sources provide lighting that is either poor in quality or poorly directed. As an example, during spinal surgery from the lumbar approach, access to the desired anatomical target area may be achieved through an angled incision on one side of the patient's midline. Light emanating from an operating microscope is static and may be poorly directed relative to the angle of surgical access. Conversely, light from a headlamp may be adjusted as a physician tilts or moves his head to redirect the output beam, but still may be blocked by various anatomical structures such as the spinous process or layers of tissue and muscle. Lighting from either source may not be adequate as the physician progresses through various phases of the procedure requiring visualization of the anatomy at varied depths from the skin-level incision.

Hand-held instruments such as suction devices are routinely used during surgical procedures such as spine surgery. These devices are typically connected to a standard suction source in the operating room, enabling the physician to dynamically and efficiently remove blood, bone fragments, or fluid previously irrigated into the surgical site. These suction devices are sometimes also used to provide low force retraction of fat, muscle, or other structures during the procedure. The surgeon holds the suction device from its proximal end, manipulating the distal portion of the suction device during the surgical procedure in order to provide suction at the desired location. Hand-held suction devices are widely available in a variety of distal tip configurations suited to various surgical applications (Frazier, Poole, Fukushima, etc).

Conventional suction devices have been constructed with fiber optic cable encased in metallic tubing and connected to metallic or non-metallic suction devices to provide some level of illumination. These devices face multiple challenges. Inefficiencies in the fiber-to-fiber coupling with high intensity light leads to light losses at the interface which produces heat. Losses are caused by non-transmissive zones between the optical fibers and Fresnel reflections at the interface. The spatial zones between the fibers are frequently the dominant cause of light loss and heat. Excess heat at the interface can cause thermal damage to the tissues and is also a fire hazard in the operating room. Some manufacturers recommend limiting the amount of light that can be transmitted to the operative device and interface, reducing the inherent heat transmission.

Therefore improved illuminated suction apparatuses are still needed. At least some of the challenges described above will be overcome by the embodiments disclosed herein.

SUMMARY OF THE INVENTION

The present invention relates generally to the field of surgical illumination and more specifically to illumination systems with integrated surgical tools.

The devices described below provide improved illumination in a surgical suction device. The illuminated suction device described below includes a metal or non-metallic suction tube having a proximal end and a distal end connected by a central portion. The proximal end of the suction tube is provided with fittings for connection to a vacuum source. The suction tube has an inner surface and an outer surface, with a layer of optical cladding having a refractive index that may be between 1.29 and 1.67 on the outer surface of the central section of the suction tube, and an illumination waveguide having a proximal end and a distal end. The illumination waveguide is formed surrounding the optical cladding on the central portion of the suction tube, and serves to conduct light around the suction tube from the proximal end to the distal end of the illumination waveguide. The illumination waveguide may have a refractive index between 1.46 and 1.7 and may have a numerical aperture between 0.33 and 0.70. An illumination input is formed into the proximal end of the illumination waveguide for conducting light from a source to the illumination waveguide.

The illuminated suction apparatus includes suction and illumination functions integrated into a hand-held device suited to meet the ergonomic needs of the physician. The hand-held, repositionable suction function already prevalently used in surgical procedures is surrounded by an illuminated waveguide which enables the physician to apply lighting directly to the desired region of the anatomy below the skin regardless of incision angle, depth, and surrounding anatomical obstructions. The illumination waveguide is a solid structure designed to specifically guide light from a high-intensity light source and is fabricated using injection molding of an optical-grade polymer with a specific index of refraction such as cyclo-olefin polymer or copolymer or any other suitable acrylic or plastic. Furthermore, the illumination waveguide can be engineered to efficiently transmit light from its distal output by sheathing or surrounding it with a second material of lower index of refraction properly coordinated to the index of refraction of the core material to preserve Total Internal Reflection (TIR). This solid-state, structure guided illumination waveguide is powered via a fiber optic cable connected to a high intensity light source such as 300 W xenon sources supplied by Luxtec, BFW, and others.

The illuminated suction apparatus may also include one or more barbs, ridges or other protrusions on the proximal end of the suction lumen enabling the connection of standard PVC surgical tubing or other suitable vacuum conduit.

The use of a generally solid waveguide for suction illumination, rather than optical fibers, eliminates losses due to the non-transmissive spaces between the optical fibers and reduces losses solely to those associated with Fresnel reflections. The marked reduction in losses associated with a fiber/fiber junction allows for high intensity light transmission to the waveguide without significant heating of the interface or need for heat sink devices or mechanisms at the interface. With a fiber to waveguide connection, light from a standard 300 watt light source can be transmitted with use of standard connectors such as ACMI, with a steady state temperature below the temperatures harmful to body tissue without design alteration. In some embodiments, a pigtail connector may be used to introduce light into the waveguide. The pigtail is a flexible optical input that is attached to a proximal portion of the waveguide. It may be a bundle of optical fibers, or a single flexible light pipe. The pigtail may be received in one or more receptacles on the proximal portion of the waveguide and bonded to the waveguide with an optical index matching adhesive. In other embodiments, the pigtail may be may be formed by overmolding the waveguide around the pigtail into a single integral part. The pigtail may flare outward to match the width of the proximal portion of the waveguide so that light is more evenly introduced into the waveguide. In still other embodiments, the pigtail may be used to provide other services to the device such as suction or electrical current. For example, the pigtail may be a flexible cable having multiple lumens. A lumen may be used to hold one or more optical fibers for delivering light to the waveguide, while another lumen may be used to provide suction to the suction tube instead of having a separate suction tube. In some embodiments, a lumen may be used to house one or more electrical conductors that supply current to the suction tube or electrodes when the device is used to deliver current to the tissue, or when the light source is a part of the device. The pigtail may have any combination of these features and is advantageous since it reduces the total number of cables required and also helps keep device profile reduced.

Use of total internal reflection and light mixing in an illumination waveguide (also referred to herein as an optical waveguide) enables control of the output light profile and enables custom illumination profiles. Microstructures such as facets, lenses and or lens arrays can be applied to any suitable surfaces of the illumination waveguide and light can be extracted incrementally along the walls of the device with injection molded structures and other suitable structures at minimal added cost. Use of sequential extraction surfaces, changes in the numerical aperture of the device as a function of position, use of extraction structures—either micro or macro structural, with or without changes in the numerical aperture, selective cladding, selective reflective coatings, etc, all can be used to shape the output profile of the waveguide to meet the design specifications or light specifications requested by the user for specific surgical suction illumination applications.

The device is meant to be disposable, fabricated out of low cost materials to enable leverage of manufacturing efficiencies through use of processes such as high-volume injection molding, over-molding, and metal & polymer extrusion. Device assembly would be engineered to minimize labor costs. A low cost, high-performance combination device provides an attractive alternative to existing discrete illumination and suction devices while minimizing incremental cost to the user.

The illuminated suction apparatus comprises a hand-held surgical device combining a high-performance illumination waveguide with suction. This device would be useful in various surgical procedures including open and minimally invasive orthopedics. The illumination waveguide may also be combined with other surgical devices such as surgical drills and probes, etc. The illumination waveguide may be fabricated with fiber optic pigtails, index matching liquid and or suction lumens.

The surgical suction field must be illuminated by the illumination waveguide while the distal suction tip is in active contact with the tissue and or fluid surface. To achieve this effect, the output light from the illumination waveguide must emanate from a point on the waveguide that is proximal to the distal suction tip of the device. Where the design configuration requires the light to exit from the waveguide proximal to the distal tip of the surgical tool, the waveguide shape may be configured to control the numerical aperture of the waveguide and thus, the divergence angle of the exiting light. Similarly, one or more refraction elements such as lenses of any suitable size may be formed in or near the distal end of the waveguide to control the light emitted from the waveguide. In surgery, when using a suction illumination device in which the output light emanates from a point proximal to the distal end of the device, a surgeon may experience difficulty due to glare from the distal tip. Thus, a light source such as an LED may be positioned adjacent the distal end of the device, or the light source may be adjacent the proximal end of the device such as in the handle, while in still other embodiments, an external light source is utilized.

In an alternate configuration, the distal tip of the suction tube may be configured to transmit light or reflect light such that the surgeon sees the distal tip of the suction as illuminated such that he/she can localize the distal tip of the suction device in their peripheral vision without directly looking at or focusing on the tip of the device. Extending a thin layer of the waveguide to the tip can provide the effect. Strategies that implement this effect include but are not limited to: (a) waveguide extended to the tip with or without surface extraction features to cause light to back reflect or scatter off the tip, (b) Use of a thin layer of optically transmissive material with high scattering coefficient to cause the suction device to glow (c) reflective surfaces applied to the outside of the central suction device (d) reflective surfaces applied with imperfections on the surface to reflect or scatter the light off the outer surface (e) use of a cladding material applied to the walls of the inner suction tube that transmits or scatters a portion of the output light, the input to the cladding being either an imperfection in the cladding or naturally occurring leakage, (f) fluorescent coating on the tip, (g) phosphorescent coatings (h) use of embedded or graded reflectors along or at the tip of the device. Alternatively, the distal tip geometry could be formed to intentionally scatter light (square edges, etc).

One or more surfaces in an optical waveguide sheath or adapters or connectors may be polarized using any suitable technique such as micro-optic structure, thin film coating or other coatings. Use of polarized light in a surgical environment may provide superior illumination and coupled with the use of complementary polarized coatings on viewing devices such as cameras or surgeon's glasses may reduce reflected glare providing less visual distortion and more accurate color rendering of the surgical site. One or more surfaces of an optical waveguide sheath may also include light filtering elements to emit light of one or more frequencies that may enhance visualization of specific tissues.

In a first aspect of the present invention, an illuminated suction device comprises a suction tube having a proximal end, a distal end, and a central portion therebetween. The proximal end is fluidly connectable to a vacuum source, and the suction tube further comprises an inner surface and an outer surface. An inner layer of optical cladding is disposed circumferentially around the outer surface of the central portion of the suction tube, and the device also includes a non-fiber optic optical waveguide. The optical waveguide has a proximal end, a distal end, and a central portion therebetween. Light is transmitted through the waveguide by total internal reflection and the light exits the distal end of the optical waveguide to illuminate a surgical field. The optical waveguide is disposed against the suction tube with the inner layer of optical cladding disposed therebetween. The device also may have an outer layer of optical cladding disposed circumferentially around the suction tube and the optical waveguide.

The suction tube may comprise a tube having a cylindrically shaped cross-section. Other cross-sections such as D-shaped, or rectangular shaped may also be employed. The distal end of the suction tube may be disposed further distally than the distal end of the optical waveguide. The device may further comprise a suction control mechanism disposed near the proximal end of the suction tube. The suction control mechanism may be adapted to control strength of suction provided by the suction tube. The suction tube may also be electrically conductive and may act as an electrode for conducting an electrical signal. A distal portion of the suction tube main remain free of cladding. A portion of the suction tube may remain unobstructed by the optical waveguide.

The inner layer of optical cladding may have an index of refraction between 1 and 1.42. The inner layer of optical cladding may form a tube having a substantially circular cross-section. The inner layer of the optical cladding may be concentric with the suction tube.

The optical waveguide may have a refractive index between 1.46 and 1.70. The optical waveguide may have a numerical aperture between 0.33 and 0.7. The distal end of the optical waveguide may comprise an array of lenses integrally formed in the distal end thereof. The array of lenses may be arranged so that at least a first lens overlaps with a second lens, and such that a spot of light emitted from the first lens overlaps with a spot of light emitted from the second lens. The distal end of the optical waveguide may comprise a plurality of microstructures for extracting light therefrom and the microstructures may be adapted to direct the extracted light to form a pre-selected illumination pattern. The optical waveguide may comprise one or more light extracting structures near the distal end of the waveguide and the light extracting structures may be disposed on an outer surface of the optical waveguide. The light extracting structures may be adapted to extract light from the optical waveguide and they may be adapted to direct the extracted light laterally and distally away from the optical waveguide to form a pre-selected illumination pattern.

The optical waveguide may have an inner curved surface and an outer curved surface, and the inner curved surface may have a radius of curvature different than that of the outer curved surface. An air gap may be maintained between the suction tube and the optical waveguide. Standoffs may be disposed on the suction tube or on the optical waveguide in order to prevent engagement of the suction tube and the optical waveguide. This helps to maintain the air gap between the suction tube and optical waveguide. The optical waveguide may comprise a polarizing element for polarizing light exiting the distal end of the optical waveguide. The distal end of the optical waveguide may not be flat. Similarly, the optical waveguide may also have a filter element for filtering light so that one or more wavelengths of light are delivered to the illumination area. In some embodiments, a barrier may be disposed between the waveguide and the suction tube and the barrier prevents fluids such as blood from wicking or otherwise traveling along the space between the waveguide and suction tube.

The outer layer of optical cladding may have a refractive index between 1.29 and 1.67. The outer layer of optical cladding may form a tube that is non-concentric with the suction tube. A portion of the outer layer of optical cladding may directly contact a portion of the inner layer of optical cladding. In still other embodiments, a layer of air may be disposed over a portion of the outer surface of the optical waveguide to form an outer layer of air cladding.

The device may further comprise a light conducting conduit that is integrally formed as a single piece with the proximal end of the optical waveguide, and the light conducting conduit may be adapted to introduce light from a light source into the optical waveguide. The light conducting conduit may comprise two light conducting conduits each having substantially rectangular cross-sections. The two light conducting conduits may be integrally formed as a single piece with the proximal end of the optical waveguide. The optical waveguide may be slidably coupled with the suction tube. Therefore, proximal movement of the optical waveguide relative to the suction tube increases spot size of the light exiting the distal end of the optical waveguide. Also, distal movement of the optical waveguide relative to the suction tube decreases spot size of the light exiting the distal end of the optical waveguide. The device may further comprise a handle coupled to the proximal end of the optical waveguide and the proximal end of the suction tube. An air gap may be disposed between the waveguide and an inner surface of the handle. Standoffs may be disposed on an inner surface of the handle or on an outer surface of the optical waveguide in order to prevent engagement of the handle and optical waveguide, thereby helping to maintain the air gap therebetween.

In still other embodiments, the waveguide may be a molded component having an elongate channel or lumen. The channel or lumen may be used to apply the suction through the waveguide and thus a separate suction tube is not required.

In another aspect of the present invention, a method of illuminating tissue in a surgical field of a patient comprises providing an illuminated suction apparatus having a suction tube and a non-fiber optic optical waveguide that transmits light therethrough by total internal reflection. The suction tube and optical waveguide are coupled together to form a single handheld instrument. The method also comprises positioning a distal end of the illuminated suction apparatus in the surgical field, and illuminating the surgical field by extracting light from the optical waveguide. Light extraction features disposed on a distal end or an outer surface of the optical waveguide are used to extract the light, and also to direct the extracted light to form a pre-selected illumination pattern in the surgical field. While illuminating the surgical field, fluid or debris may be suctioned from the surgical field with the suction tube.

The illuminated suction apparatus may comprise an inner layer of optical cladding that is disposed around the suction tube. The inner layer of optical cladding may be disposed between the suction tube and the optical waveguide. An outer layer of optical cladding may be disposed around both the suction tube and the optical waveguide.

The distal end of the illuminated suction apparatus may be positioned into engagement with the tissue while a distal end of the optical waveguide does not engage the tissue. A distal end of the optical waveguide may comprise an array of lenses integrally formed therein. Illuminating the surgical field may comprise projecting a spot of light from each lens in the array such that at least a first spot of light overlaps with a second spot of light in the surgical field. Illuminating the surgical field may also comprise extracting light from the optical waveguide with one or more light extracting structures. The extracted light may be directed laterally and distally away from the optical waveguide. Illuminating the surgical field may comprise illuminating the surgical field with polarized light. Illuminating the surgical field may comprise filtering light delivered by the waveguide so that one or more wavelengths of light are delivered to the surgical field.

The method may further comprise controlling suction strength provided by the suction tube with a suction control mechanism. The method may also comprise stimulating the tissue with electrical current delivered by the suction tube. The optical waveguide may be slidably positioned relative to the suction tube thereby allowing an increase or decrease in spot size of the extracted light on the tissue.

In still another aspect of the present invention, a method of manufacturing an illuminated suction apparatus comprises providing a suction tube having a proximal end, a distal end, a central section disposed therebetween, an inner surface and an outer surface, and providing a non-fiber optic optical waveguide having a proximal end, a distal end, and an outer surface. The optical waveguide transmits light therethrough by total internal reflection. An inner layer of optical cladding is fit over the outer surface of the central section of the suction tube, and the optical waveguide is coupled with the suction tube with the inner layer of optical cladding disposed therebetween. An outer layer of optical cladding is fit over the outer surface of the suction tube and over the outer surface of the optical waveguide.

The suction tube may comprise a tube having a circular cross-section. The optical waveguide may have a first curved side with a first radius of curvature and a second curved side with a second radius of curvature. The first radius of curvature may be different than the second radius of curvature. Fitting the inner layer may comprise heat shrinking the inner layer onto the suction tube. Coupling the optical waveguide with the suction tube may comprise disposing the suction tube in an elongated open or closed channel disposed along the optical waveguide. Fitting the outer layer may comprise heat shrinking the outer layer onto the suction tube and the optical waveguide.

In yet another aspect of the present invention, a hand held illuminated suction device comprises a suction tube, a non-fiber optic optical waveguide and optical cladding. The suction tube has an inner surface, and outer surface, a proximal portion and a distal portion. The proximal portion is configured to be fluidly coupled to a vacuum source, and the distal portion is configured to remove fluid or debris from a surgical field. The non-fiber optic optical waveguide has an outer surface, a proximal region and a distal region. The optical waveguide is disposed over the outer surface of the suction tube, and light is transmitted from the proximal region of the optical waveguide toward the distal region thereof by total internal reflection. The light is emitted from the distal region of the optical waveguide and directed distally to illuminate the surgical field. The optical cladding is disposed over the outer surface of the optical waveguide and prevents or minimizes contact between the optical waveguide and the fluid, the debris, or tissue in the surgical field. Thus, the optical cladding promotes total internal reflection of the light transmitted through the optical waveguide. The one or more standoffs are disposed between the optical waveguide and the suction tube, and they prevent engagement between a portion of the suction tube with a portion of the optical waveguide thereby maintaining an air gap therebetween. The air gap facilitates total internal reflection of the light through the optical waveguide.

The device may also have a suction hole and a plurality of fins that are both adjacent the distal portion of the suction tube. The plurality of fins may be configured to prevent the tissue in the surgical field from occluding the suction hole. The suction tube may conduct electricity, and thus the suction tube may act as an electrode for delivering current to the tissue in the surgical field without requiring separate electrodes. Additionally, when the suction tube serves as the electrode, because it is conductive, conductor wires may not be required to run alongside the entire suction tube since the conductor wire may be coupled to a proximal portion of the suction tube. Any portion of the suction tube may be insulated with a non-conductive layer such as heat shrink so that the current exits the suction tube only at a desired point along the suction tube. Furthermore, if the suction tube is malleable, it may be bent or otherwise deformed into any desired shape to deliver suction, illumination, and/or current to a desired position in the surgical field. One or more electrodes may be coupled to the suction tube. The electrodes may be configured to deliver current to the tissue in the surgical field.

The optical waveguide may have a cross-section that changes from the proximal region thereof toward the distal region thereof. The optical waveguide may have a width and a thickness and the width may increase or decrease from the proximal region thereof toward the distal region thereof. The thickness may similarly increase or decrease from the proximal region toward the distal region. The illuminated suction apparatus may have an array of lenses disposed on the distal region of the optical waveguide, and the array of lenses may be configured to project the light into a pattern in the surgical field. The light projected from each lens in the array may form an illumination pattern, and the lenses may be arranged to have a pitch so that the illumination patterns overlaps with one another. The light may emanate from a region of the optical waveguide that is proximal of the distal portion of the suction tube.

The optical cladding may comprise an elongate molded polymer element that may be rigid or flexible. The elongate molded polymer element may have an elongate concave region that is configured to receive the optical waveguide. The handle may be disposed over the elongate molded polymer element.

The illuminated suction apparatus may further comprise a first handle that is coupled to the proximal portion of the suction tube and also coupled to the proximal region of the optical waveguide. The first handle may be ergonomically configured to fit in an operator's hand. The first handle may be disposed around the outer surface of the optical waveguide with an air gap disposed therebetween. The air gap promotes total internal reflection of the light passing through the optical waveguide. The device may also have a pistol grip handle that is fixedly or removably coupled to the first handle. The device may also have a cradle that is configured to receive the suction tube. The device may have a suction control mechanism that is adjacent the proximal portion of the suction tube. The suction control mechanism may be adapted to control suction strength provided by the suction tube.

In still another aspect of the present invention, a method for illuminating tissue in a surgical field of a patient comprises providing an illuminated suction apparatus having a suction tube and a non-fiber optic optical waveguide. The suction tube and the optical waveguide are coupled together to form a single hand held instrument. The method also includes maintaining an air gap between the suction tube and the optical waveguide. The air gap promotes total internal reflection of light passing through the optical waveguide. Fluid and debris in the surgical field are prevented from contacting the optical waveguide by providing an optical cladding disposed over the optical waveguide. The optical cladding also promotes total internal reflection of the light passing through the optical waveguide. The distal region of the illuminated suction apparatus is advanced into the surgical field, and the surgical field is illuminated with light from the optical waveguide. The light is directed to the surgical field by an array of lenses disposed on a distal region of the optical waveguide. The directed light forms a pre-selected illumination pattern in the surgical field. While the surgical field is being illuminated, debris or fluid such as blood may be removed from the surgical field with the suction tube.

The optical cladding may comprise an elongate molded polymer element that has an elongate concave region configured to receive the optical waveguide. Illuminating the surgical field may comprise positioning the distal region of the optical waveguide in the surgical field without engaging the tissue. Illuminating the surgical field may comprise projecting the light from each lens in the array into an illumination pattern, and the lenses may be arranged to have a pitch such that the illumination patterns overlap with one another. Suction strength provided by the suction tube may be controlled by providing a suction control mechanism. Electric current may be delivered from the suction tube or from one or more electrodes coupled to the suction tube to stimulate the tissue.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 is a side view of an alternate illumination conduit.

FIGS. 6A, 6B and 6C are various cross-section views of the alternate illumination conduit of FIG. 6.

FIG. 6D is a perspective view of access port of the alternate illumination conduit of FIG. 6.

FIGS. 30A-30D illustrate exemplary embodiments of electrode tips.

DETAILED DESCRIPTION OF THE INVENTION

Figure 1:
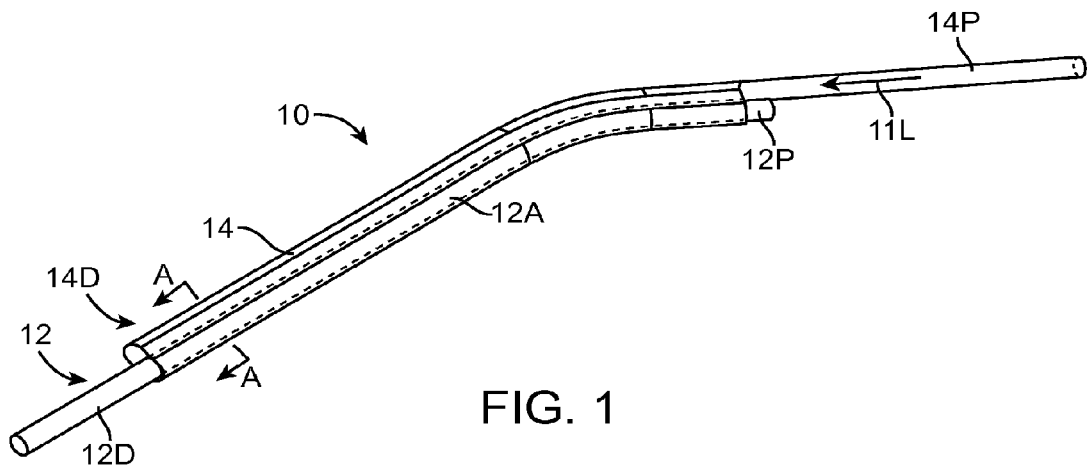
FIG. 1 is a perspective view of an illuminated suction apparatus.
Figure 1A:
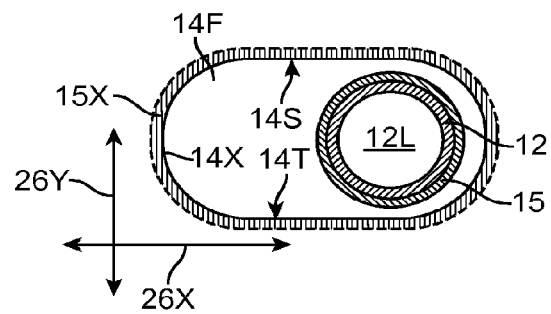
FIG. 1A is a cross-section view of the illuminated suction apparatus of FIG. 1 taken along A-A

Referring to FIGS. 1, 1A, 2 and 2A, illuminated suction apparatus 10 includes suction tube 12 enclosing a suction lumen 12L. The suction tube in this embodiment or any of the embodiments disclosed herein may be made of any suitable material such as a metal like aluminum, stainless steel, or polymers such as acrylic, ABS, PVC, and the like. The cross-section of this suction tube or any suction tubes disclosed herein may be circular, non-circular, D-shaped, rectangular, oval, or any other geometry may be used. Illumination waveguide 14 is secured over cladding layer 15 on central portion 12A of suction tube 12 leaving input or proximal portion 12P and distal portion 12D exposed. Illumination waveguide 14 may have one or more sides, surfaces or other portions that are configured such as flat side 14S or side 14T to optimize light mixing as light 11L travels from illuminator input end 14P to exit through light output face, or distal face 14F on output end 14D.

Illumination waveguide 14 is made of an optical grade engineering thermoplastic such as cyclo olefin polymer which efficiently transmits light. Any other suitable material such as Cyclic Olefin Copolymer, Polycarbonate, Acrylic and or TPC may also be used. Thus, the waveguide is preferably a single piece, formed from a homogenous material. It may also be flexible or rigid and self-supporting and thus is not a fiber optic which is unable to support itself. The angles and bends of the waveguide structure are engineered so light transmits through the waveguide via total internal reflection (TIR). The side walls and other features have angles and flat areas such that light is mixed and not allowed to escape until it reaches the distal end 14D of the waveguide and exits with a selected uniformity. Light that is reflected by TIR is internally reflected with high efficiency (nearly 100% efficiency). Suction tube 12 introduces a curved interface with illumination waveguide 14 that changes the angle of reflection and creates unwanted scatter of the light. Thus an uncoated or untreated suction tube will cause a small portion of light to be lost to absorption and or scattering at each reflection, ultimately resulting in poor light transmission efficiency. In order to preserve TIR through the waveguide, cladding material 15 with a specific index of refraction is placed between the suction tube and the waveguide. TIR can also be potentially disrupted by blood or foreign matter from the surgical site coming into contact with exterior exposed surface 14X of illumination waveguide 14. Exterior cladding layer 15X having a specific refractive index can also be attached to the outside of the waveguide. The waveguide material may or may not completely surround suction tube 12 in order to provide an illumination pattern from distal end 14D unobstructed by a shadow from the metallic or malleable plastic suction tube. The waveguide and TIR-preserving materials are chosen to provide an optimized light exit angle, total light output, and illumination suited to properly visualize the surgical site. Suction tube 12 could be treated (for example anodized in the case of aluminum) in order to reduce glare or reflections resulting from interaction with light output from the illuminator.

Figure 1B:
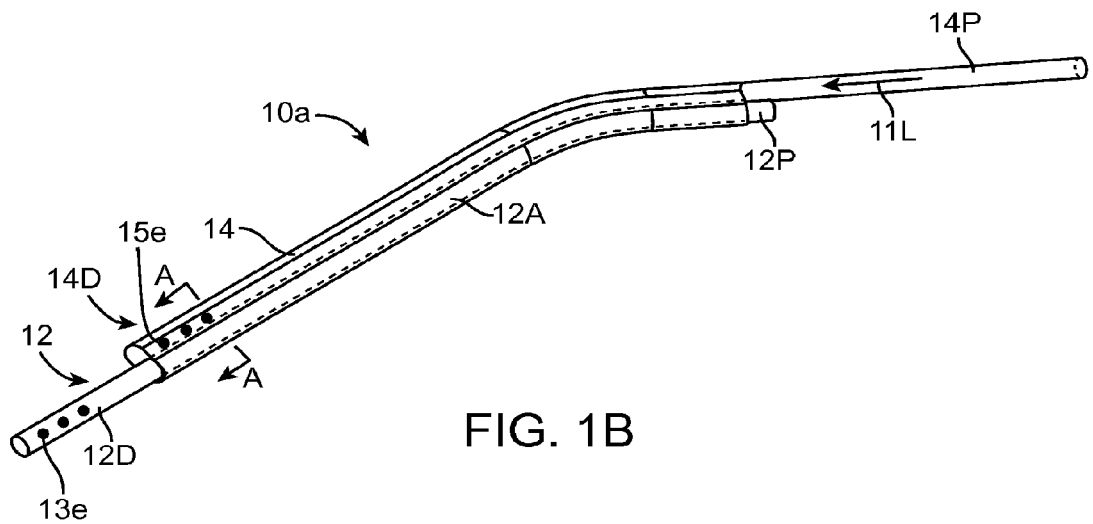
FIG. 1B illustrates an exemplary embodiment of an illuminated suction apparatus with electrodes.
Figure 2:
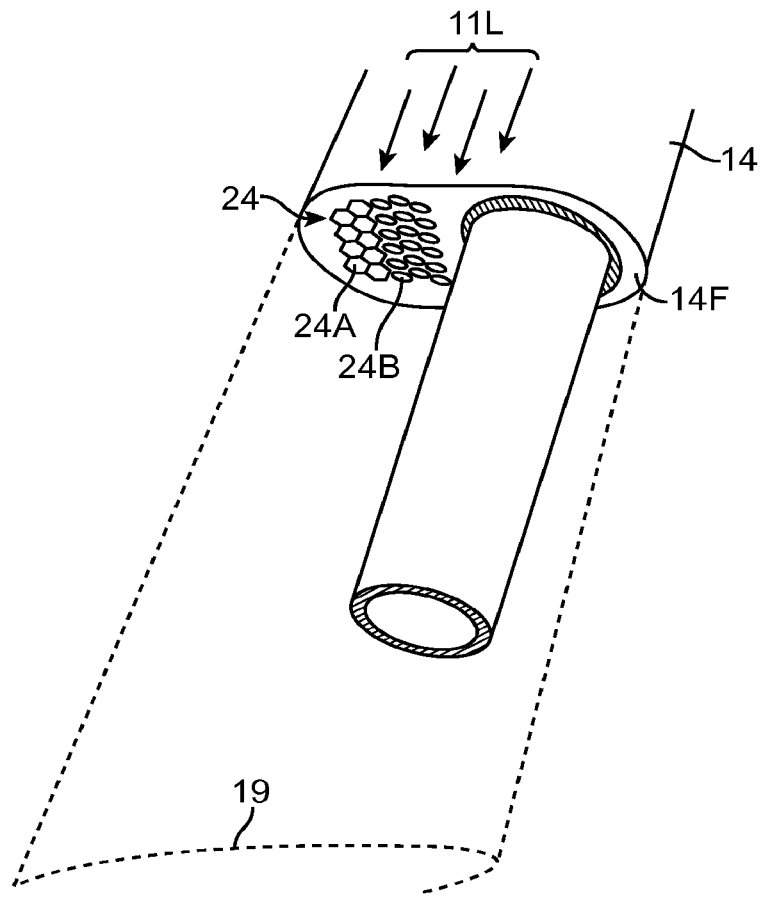
FIG. 2 is a close up perspective view of the distal end of the illuminated suction apparatus of FIG. 1.
Figure 2A:
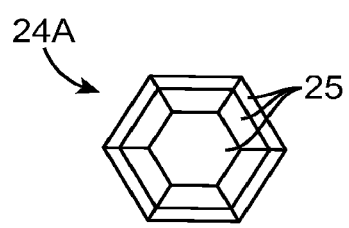
FIG. 2A is a close up view of a single lens from the lens array of FIG. 2.

FIG. 1B illustrates an alternative embodiment of an illuminated suction apparatus 10a having electrodes. One or more electrodes 13e may be disposed on a distal portion of the suction tube 12, and/or one or more electrodes 15e may be disposed on a distal portion of the waveguide 14. The electrodes allow the illuminated suction apparatus to be used as a probe for stimulating various tissues such as nerves, or for cauterizing tissue. Wires or other conductors may couple the electrodes to the proximal end of the illuminated suction apparatus 10a which may then may be coupled with an energy source that provides the current delivered by electrodes 13e or 15e. The electrodes may be attached to the outer surface of the suction tube, or a portion of the outer cladding 15 may be removed to allow the metal suction tube to be exposed and used as an electrode. Thus, the suction tube itself may be used as a conductor and electrode. Similarly, electrodes may be attached to the outer surface of the waveguide, or a portion of the cladding 15X may be removed to allow portions of the waveguide to be exposed and used as an electrode if conductive, or the electrodes may be coupled to the waveguide. The illuminated suction apparatus may then be operated in monopolar or bipolar mode.

FIGS. 30A-30D illustrate other exemplary embodiments of electrode tips that may be formed into the suction tube. For example, FIG. 30A illustrates suction tube 3002 having a rectangular shaped electrode 3004a extending distally past the distal edge of the suction tube. The width of the electrode 3004a may be the same width as the suction tube, or it may be greater or less. Additionally, the length of the electrode may be varied as required. For example, FIG. 30B illustrates a similar rectangular shaped electrode 3004b but that extends distally away from the suction tube less than the previous embodiment. FIG. 30C illustrates an electrode 3004c that is narrower than the suction tube 3002 and it may be trapezoidally shaped, while in FIG. 30D, the electrode 3004d is triangular shaped. The electrodes may be formed by removing material from the suction tube so that a single piece, integral device is formed, or the electrodes may be welded or otherwise attached to the suction tube.

In an alternate configuration, distal face 14F of waveguide 14 may include any suitable surface treatment to control how light 11L forms illumination pattern 19. One or more lenses, or lens arrays such as lens array 24 may be formed on distal face 14F. Suitable optical features such as lens array 24 may include lenses of identical, similar or different shapes and sizes to produce the desired illumination pattern or patterns. Combinations of lens shapes and radii may be used to optimize lens arrangement on the distal or output face of the waveguide. The lens array may include lenses on any portion of distal face 14F. Distal face 14F is generally planar and may be described with respect to orthogonal axes 26X and 26Y. Individual lenses of lens array 24 may also be oriented differently, i.e. have a different pitch, relative to planar axes 26X and 26Y. In one exemplary embodiment, a plurality of lenses is disposed on the distal face 14F. Light is projected from each lens distally toward the surgical field in an illumination pattern. The pitch of the lenses may be adjusted such that the illumination patterns are discrete and separate from one another, or the pitch of the lenses may be adjusted such that the illumination patterns overlap with one another. Overlapping illumination patterns help eliminate non-uniform illumination that results from optical defects in the lenses and/or waveguide. Optical defects may be caused by parting lines, gates, scratches, etc. in the optical waveguide and lenses. By overlapping illumination patterns, the non-uniformities are "covered up" or "washed out" by other illumination patterns provided by adjacent lenses in the lens array. Additional details about this feature are disclosed below.

Individual lenses such as lens 24A may adopt any suitable geometry and may be curved or faceted with one or more facets such as facets 25. Polygonal shapes such as lens 24A allow the lenses to be located immediately adjacent to each other eliminating undirected light leakage between the lenses.

In still other embodiments, the distal end of the waveguide may be flat or it may be curved (convex or concave) in order to help shape and direct light to the surgical field. Polarizing elements or filters may also be coupled to the distal end so that the waveguide delivers polarized light to the surgical field which may be advantageous in preferentially visualizing certain tissues. The polarizing elements may also be a wire grid polarizer.

Figure 14:
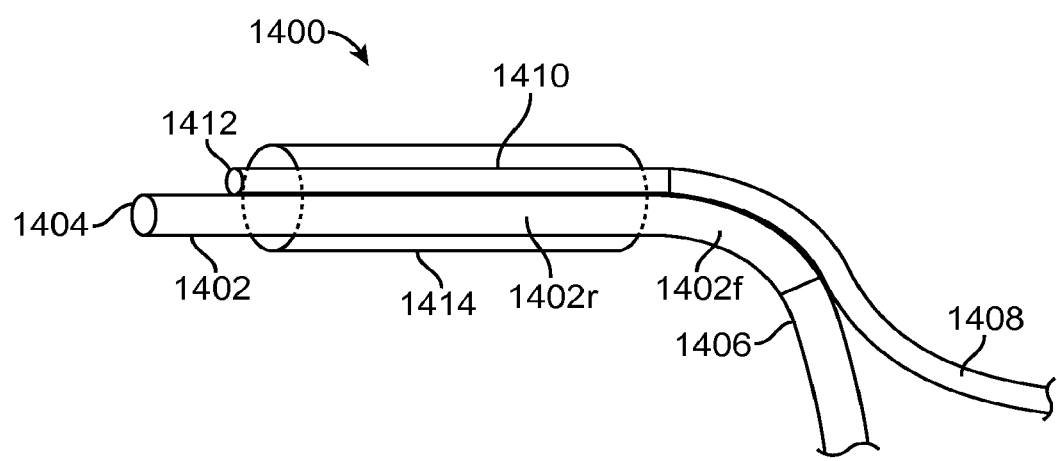
FIG. 14 is another exemplary embodiment if an illuminated suction apparatus.
Figure 14A:
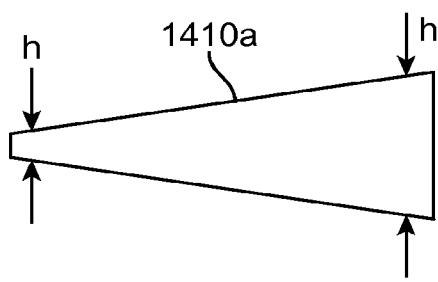
FIGS. 14A-14B illustrate exemplary geometries of a waveguide.
Figure 14B:
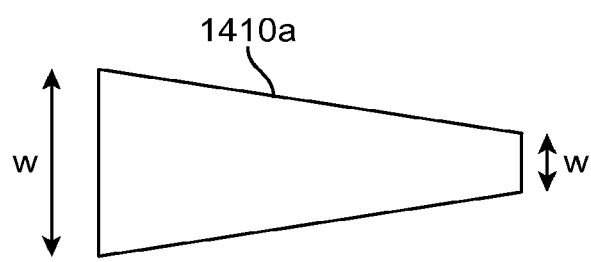

FIG. 14 illustrates another exemplary embodiment of an illuminated suction apparatus 1400. The illuminated suction apparatus 1400 includes an illumination waveguide 1410 disposed adjacent a suction tube 1402. The suction tube may be formed of malleable metal or another malleable material such that it has a straight relatively rigid distal section 1402r, and a pre-bent flexible proximal section 1402f. The suction tube 1402 may be joined to a flexible tubing 1406 that fluidly connects the suction tube 1402 to a vacuum source (not illustrated) and thus the distal tip 1404 of the suction tube 1402 may be used to remove fluid or other material from the surgical field. Illumination waveguide 1410 is preferably a non-fiber optic waveguide (preferably as are any of the waveguides described herein). The waveguide may be cylindrical as illustrated in FIG. 14, or it may have other profiles such as a square cross-section, rectangular, oval, elliptical, ovoid, etc., or any of the other geometries described herein. The pre-bent malleable section 1402 allows a surgeon or other operator to bend the suction device so that it can access various surgical sites and accommodate differing anatomies. Another possible cross-section for the illumination waveguide is illustrated in FIGS. 14A-14B where the height h of the waveguide 1410a tapers down such that the proximal end is higher than the distal end. Also, the width of the waveguide 1410a may also increase from the proximal end to the distal end as seen in FIG. 14B. This geometry results in a trumpet shaped waveguide having a lower profile so that it may fit in a smaller incision and take up less space in the surgical field.

In the embodiment illustrated in FIG. 14, the illumination waveguide therefore has a flat upper surface and a flat lower surface, as does the suction tube 1402. Therefore, the bottom surface of the illumination waveguide lays flush against the upper surface of the suction tube. An outer sheath 1414 such as heat shrink may then be used to hold the illumination waveguide and suction tube together. The outer sheath 1414 may be selected to have desirable optical properties in order to minimize loss of light. For example, FEP heat shrink has a desirable index of refraction so that light is transmitted along the waveguide 1410 and then extracted from the distal portion 1412 using any of the extraction features described herein. The outer sheath 1414 may also be a tight fitting polymer sheath that is stretched over the waveguide and suction tube, and may not be heat shrink tubing. Additionally, a separate layer of cladding such as heat shrink tubing or tightly fitting tubing (not illustrated) that can be stretched may be disposed over the suction tube in order to minimize light loss caused by contact between the suction tube and the illumination waveguide. The separate layer of cladding may be FEP tubing or any of the other materials described herein, and preferably is disposed entirely around the circumference of the suction tube. A fiber optic cable 1408 couples the illumination waveguide with an external light source (not shown). The fiber optics cable in this embodiment is preferably integral with the waveguide (e.g. injection over-molded together) so as to be fixedly connected to one another. In alternative embodiments, the fiber optic cable is releasably connected to the waveguide. By joining the fiber optic cable 1408 to the waveguide near the connection point between the suction tube and flexible tubing 1406, allows the surgeon or operator to easily flex or otherwise manipulate the suction tube without interference from the fiber optic cable. The fiber optic cable 1408 may be coupled with the waveguide 1402 such that when the malleable bent portion 1402 is bent, the fiber optic cable 1408 bends with the suction tube 1402f, or in other embodiments, the fiber optic cable 1408 need not be coupled with the bent malleable portion 1402f and may hang freely and independently of the suction tube.

Figure 15A:
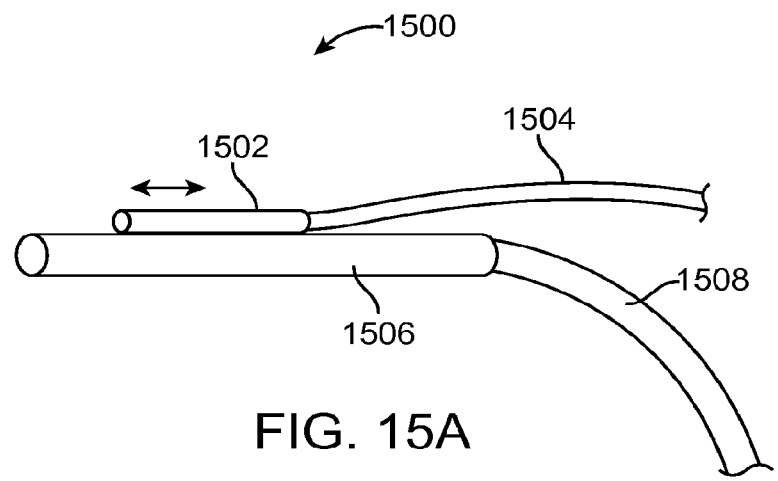
FIGS. 15A-15C illustrate an exemplary embodiment of an illuminated suction apparatus with an adjustable illumination waveguide.
Figure 15B:
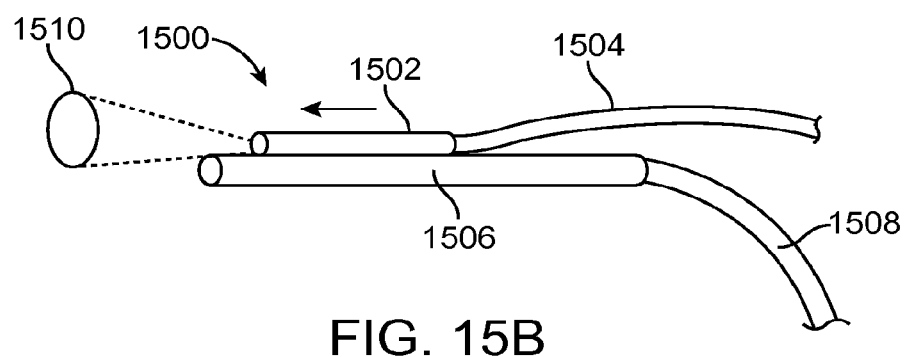
Figure 15C:
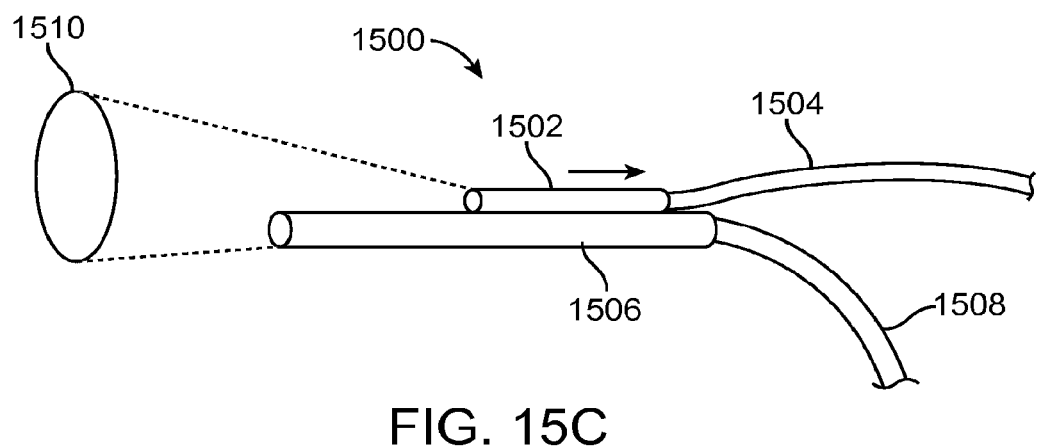

In any of the embodiments disclosed herein, the waveguide position along the suction tube may be adjustable. For example, in FIG. 15A illuminated suction apparatus 1500 includes an illumination waveguide 1502 coupled to a fiber optic cable 1504. The illumination waveguide 1502 is slidably disposed over suction tube 1506 which is connected to flexible vacuum tubing 1508. The waveguide may slide proximally or distally relative to the suction tube 1506 and this permits regulation of light output spot size and brightness in the surgical field. In FIG. 15B, the waveguide 1502 is advanced distally relative to the suction tube 1506 thereby resulting in a smaller spot of light 1510 and a more brightly lit distal tip of the suction tube and surgical field. In FIG. 15C, the illumination waveguide is retracted proximally relative to the suction tube and thus the light spot size 1510 is larger and more diffuse than in FIG. 15B and therefore less brightly lighting up the distal tip of the suction tube as well as less brightly illuminating the surgical field. The waveguide 1502 in FIG. 15A may have a circular cross-section or it may have other cross-sections such as flat, curved, rectangular, or any of the cross-sections disclosed herein. In some embodiments, the waveguide has a concave inner surface that forms a saddle for receiving the suction tube, and a convex outer surface. This allows the waveguide to be mated with the suction tube with a low profile, as discussed herein with respect to FIG. 16.

Figure 3:
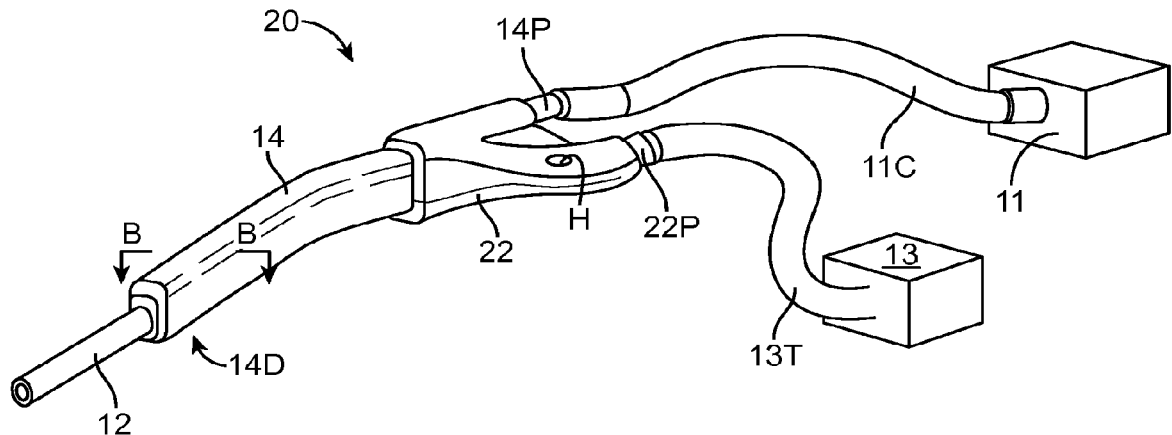
FIG. 3 is a perspective view of an illuminated suction apparatus with a handle.

Referring now to FIG. 3, Light 11L from light source 11 is conducted to the illumination waveguide using any suitable apparatus such as fiber optic cable 11C and is then conducted through waveguide 14 and exits from any appropriate structure or structures on or near distal end 14D of the waveguide. Alternatively, in this or any embodiment herein, the light source, such as an LED could be integrated into the suction handle eliminating the need for a fiber optic connection, or the LED may be disposed distally, adjacent the distal tip of the device. Vacuum from suction source 13 is conducted to illuminated suction apparatus 20 using any suitable suction tube such as tube 13T which is connected to vacuum input 22P. The vacuum available at the distal end of suction tube 12 may be controlled by covering all or a portion of suction hole H in handle 22.

Illuminated suction apparatus 10 may be integrated into a handle such as handle 22 made of relatively low-cost engineering plastic such as ABS or polycarbonate. Handle 22 may be formed from two or more components that could be separate injection molded components designed to be snap fit, glued, or ultrasonically welded together. Alternatively, the handle could be formed over an illuminated suction apparatus such as apparatus 10 through an over-molding process. The proximal portion of the combined device such as illuminated suction apparatus 20 would also contain a hole, hole H, properly positioned to allow the surgeon to enable the suction function by obstructing all or a portion of the hole with a finger; the hole communicates with the suction pathway in the device, disabling suction by creating a "suction leak" when it is not blocked. Varying the hole geometry, as in the case of Fukijima suction, affords finer modulation of the suction function. The proximal end of handle 22 may also contain inputs for a traditional fiber optic cable to be attached to illumination waveguide 14, such as a male ACMI connection or other suitable connector, and a vacuum port such as vacuum port 22P which may be a barbed fitting suitable for standard flexible suction PVC suction tubing of various sizes to be attached. The fiber optic cable is attached to a high-intensity light source such as light 11. Suction tube 13T is attached to any standard vacuum source in the OR such as a waste collection container with integrated vacuum pump such as vacuum source 13.

Figure 4:
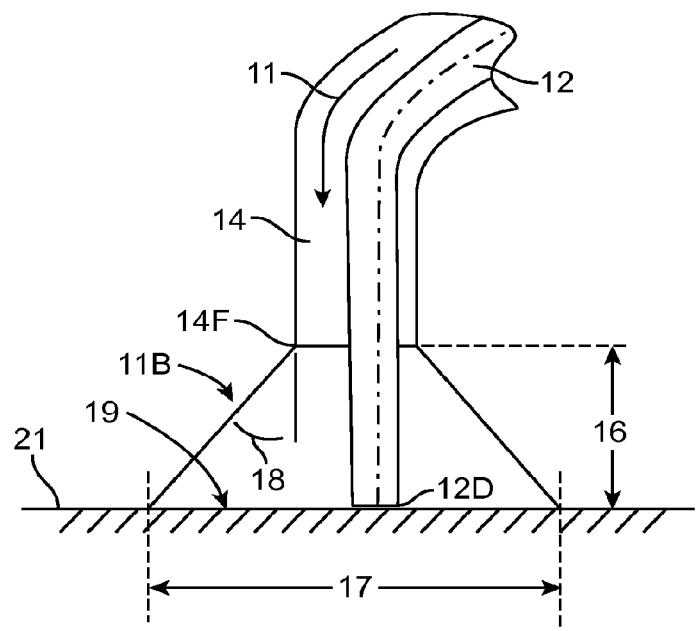
FIG. 4 is a cross section view of the distal end of the illuminated suction apparatus of FIG. 3 taken along B-B.

Referring now to FIG. 4, light beam 11B exits waveguide distal face 14F at a specific angle based on the optical properties such as the numerical aperture (NA) of the input source, index of refraction of the material, and shape of the waveguide. Light pattern 19 cast onto the target surgical field is optimized based on the specific distance 16 the illuminator is set back from the distal tip 12D of the suction tube. For a given light source configuration, divergence angle 18 of light beam 11B results in a specific illumination pattern 19 with a total light output and illumination size 17 at any target plane normal to the illuminator such as plane 21. The plane at the distal tip of the suction tube is of particular interest, since the physician will place the distal tip at the desired surgical target to enable suction or retract tissue.

Figure 4A:
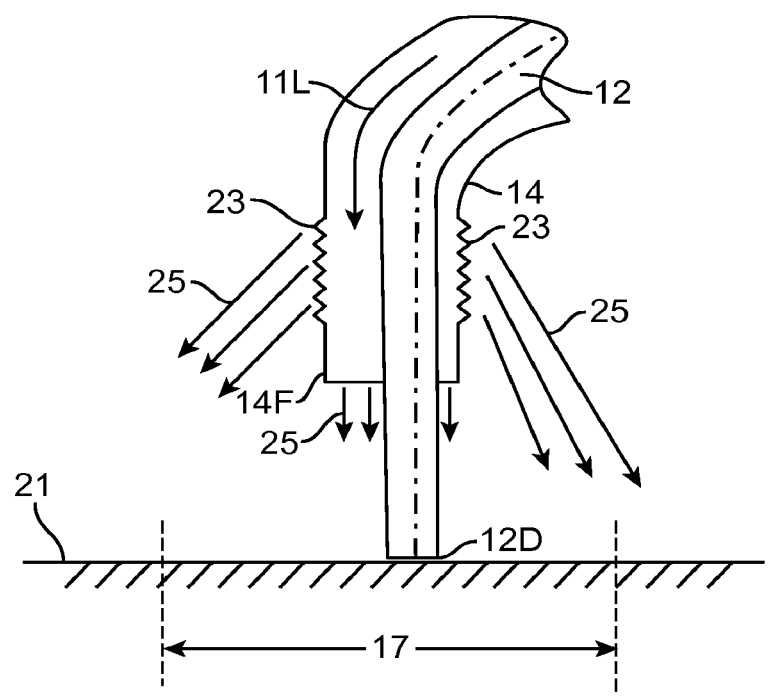
FIG. 4A illustrates an exemplary embodiment of light extraction from a lateral surface of the illuminated suction apparatus.

FIG. 4A illustrates an alternative embodiment of an illuminated suction apparatus having light extraction features 23 on a lateral surface of the illumination waveguide that extract light 25 and direct the light 25 laterally and distally toward the surgical field. This may feature may be used alone or in combination with the distal features previously described above. The extraction features may include prisms, lenses, lenslets, multiple facets, or other surface features known in the art that extract light from the waveguide and direct the light to a desired area in a desired pattern. The extraction features may be disposed in a discrete area to extract light only from that area, or the extraction features may be disposed circumferentially around the waveguide so that a uniform ring of light emits from the waveguide. Using both lateral extraction features and distal light features allows diffuse light to emit from the lateral surfaces of the waveguide while more focused light can be emitted from the distal tip of the waveguide.

Figure 5:
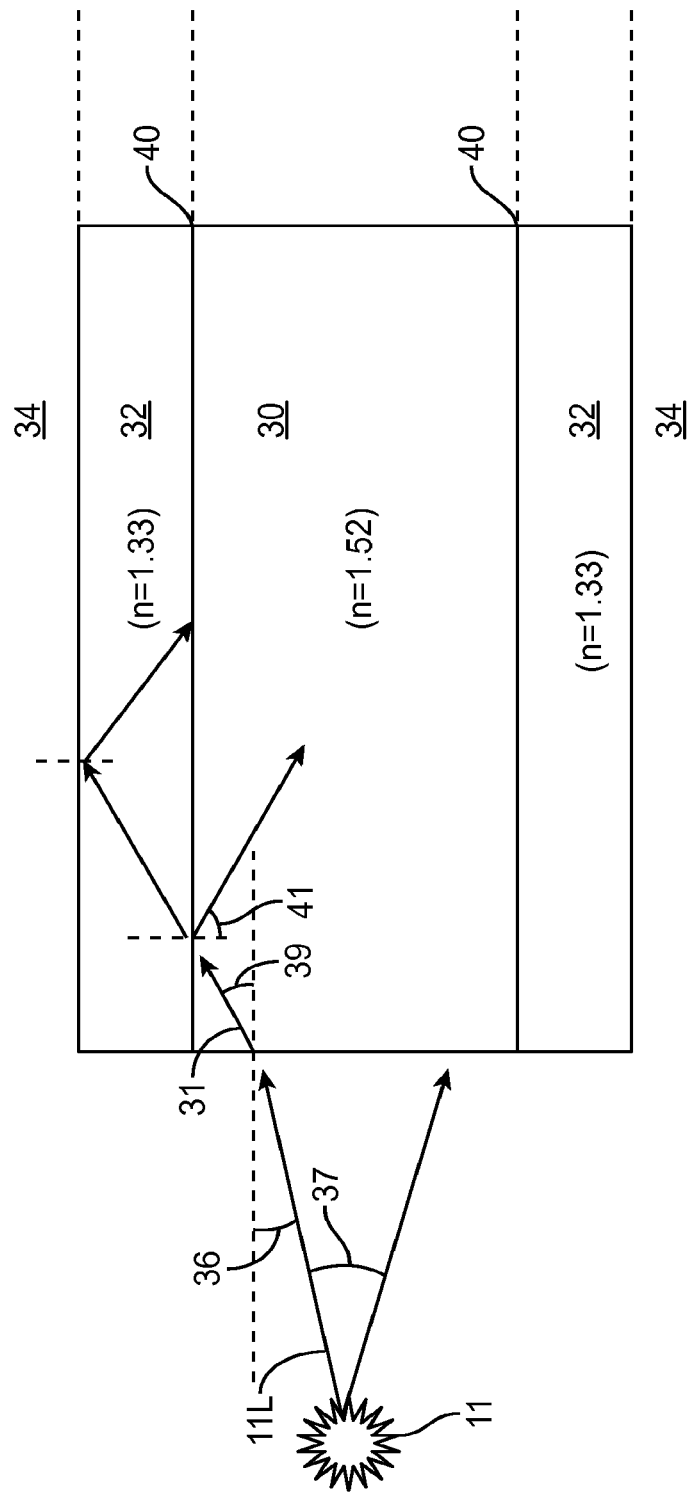
FIG. 5 is a cross section view of an illumination conduit input according to the present disclosure.

Referring now to FIG. 5, light source 11 is transmitting light 11L into cyclo olefin polymer core 30 with refractive index 1.52, fluorinated ethylene propylene (FEP) cladding 32 with refractive index 1.33, and an external environment 34 surrounding cladding 32. Light source 11 is assumed to be in air with a refractive index of 1 and a numerical aperture (NA) of 0.55 which corresponds to a half-cone angle, angle 36, of 33.4 degrees. The NA of source 11 is the angle of incidence on the core when light 11L is coupled in which corresponds to angle 37. Internal light rays 31 initially enter core 30 at the half cone angle of 33.4 degrees and are refracted at an angle of 21.2 degrees, internal refraction angle 39 when they pass into core 30. Internal light 31 then intersects core-cladding boundary 40 at an angle of 68.8 degrees which is angle 41. As long as angle 40 is greater than the critical angle determined by the core and cladding indexes, light 31 will undergo TIR and none of light 31 will be transmitted into the cladding. In this case (n-core=1.52 & n-cladding=1.33) the critical angle is 61.0 degrees.

This ray trace can be worked backwards from the critical angle to determine the maximum source NA that will still allow for all light to undergo TIR at the core-cladding boundary. If reflection angle 41 is 61.0 degrees which corresponds to the critical angle for the selected core and cladding, then internal refraction angle 39 is 29 degrees which means that angle 37 must be 47.4 degrees. From 47.4 degrees, the source NA is calculated to be 0.74. Therefore, when using the cyclo olefin polymer/FEP combination, an input source with a much higher NA/Efficiency can be used.

If the source NA is such that all the light coupled into the waveguide undergoes TIR at the core-cladding boundary, then no light is propagating in the cladding and the environment index does not affect the waveguide transmission and no light is hitting the cladding-environment boundary. The data in the following table shows how the critical angle changes at the core-cladding boundary as the cladding index changes from 1.0 to 1.46 for a cyclo olefin polymer core (n=1.52). This is particularly relevant when designing refractive structures. Knowing the critical angle ahead of time, based on the environment or cladding, the structures can be designed to preferentially leak light from the illumination conduit.

| Cladding Index | Core-Cladding Critical Angle (degrees) |
|---|---|
| 1.00 | 41.1 |
| 1.10 | 46.4 |
| 1.20 | 52.1 |
| 1.30 | 58.8 |
| 1.40 | 67.1 |
| 1.417 | 68.8 |
| 1.42 | 69.1 |
| 1.44 | 71.3 |
| 1.46 | 73.8 |

When using FEP as a cladding with cyclo olefin polymer, the critical angle is smaller than the angle from the 0.55NA (68.8 degrees). If no cladding is used, at the index of 1.417 and higher, the critical angle equals to the input angle causing light leakage because TIR is not maintained. Moreover, the combination of a cyclo olefin polymer core with FEP cladding allows the use of an input source with NA exceeding 0.55. The input source would enable greater light capture from a source due to the larger acceptance angle and provide more light through the illumination conduit assuming constant transmission efficiency. Understanding the critical angles of FEP and open environment, structures can be designed more accurately to extract the light from the illumination conduit.

Any suitable cladding materials such as FEP can be applied to central portion 12A of suction tube 12 through methods such as manual or semi-automated shrink-application of oversized FEP with a heat gun or focused heat from a hot-box nozzle, leveraging FEP's characteristic shrink ratio. Any other technique of a cladding such as FEP may be used such as applying a liquid coating or vapor deposition of FEP to central portion 12A or any other suitable surface to be clad. Suction tube 12 with integrated cladding 15 can then have illumination waveguide 14 insert-molded (via conventional high-volume injection molding) and waveguide 14 will able to maintain total internal reflection. Use of cladding 15 between suction tube 12 and illumination waveguide 14 enables the suction tube to be formed of any suitable material such as metal or plastic. The choice of the plastic material for the suction tube needs to be such that the index of that material is below 1.42 for use with a waveguide having an index of 1.52 to maintain the differential at the interface of the suction tube and the waveguide. However, use of plastic may create challenges with injection molding processes which require relatively high temperatures and pressures inside of the molding cavity. Alternatively the device can be manufactured such that illumination waveguide 14 is formed with an internal lumen with no additional suction conduit miming through it. The challenge posed by this approach is the potential light transmission efficiency losses stemming from evacuating biological material (blood, etc) through the lumen and making contact with the internal surface of the illumination waveguide lumen throughout the procedure.

Cladding with an index of 1.33 shows no light transmission dependence on the refractive index of the surrounding environment or the cladding thickness when used with an illumination waveguide having a refractive index at or near 1.52. For a cladding with an index of 1.33, the light coupled into the illumination waveguide is constrained to the core due to total internal reflection at the core-cladding interface. Thus, there is no light propagating through the cladding, making the cladding-environment boundary condition a negligible factor in transmission. Teflon FEP with an index of 1.33 used as a cladding material with a cyclo olefin polymer core with index 1.52, shows no dependence on cladding thickness in three representative simulated surgical environments.

Figure 17:
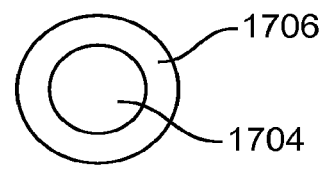
FIG. 17 illustrates another cross-section of an illuminated waveguide apparatus.

While preferred embodiments use heat shrink as the cladding over the suction tube and/or over the waveguide, in other embodiments, a low index of refraction polymer may be injection molded or otherwise formed over the waveguide. FIG. 17 illustrates an illumination waveguide 1704 having such a polymer 1706 molded thereover. This allows the polymer to minimize light loss from the waveguide, and also allows the polymer 1706 casing to be used for attaching to the suction tube or other surgical instruments. For example, the two may be bonded together, solvent bonded, welded, or otherwise joined together. In still other embodiments, snaps or other coupling mechanisms may be joined to the polymer and suction tube forming a snap fitting. Any number of coatings or claddings may be used in the previous embodiment, or in any of the embodiments described elsewhere in this specification. The coatings or claddings may be used to enhance total internal reflection, or the coatings or claddings may be used for to impart desired optical properties to the light (e.g. polarize the light delivered to the surgical field, etc.), or the coatings or claddings may be used to provide a protective barrier against damage to the waveguide. Multiple layers of coatings or claddings may be used. For example, a low index of refraction coating or cladding may be applied to the waveguide to help with total internal reflection, and then a protective layer may be disposed thereover in order to help minimize damage to the waveguide.

An illumination waveguide formed from material with a refractive index of 1.46, showed light transmission dependence on both cladding thickness as well as the external environment. This is a result of introducing light into the illumination waveguide at an NA of 0.55. Under this condition, light enters the core at an angle that is less than the critical angle of the core-cladding boundary, resulting in light propagating into the cladding. Since light propagates through the cladding, the cladding-environment boundary condition (critical angle) is a factor in the light transmission. Due to light propagating through the cladding, the cladding thickness also affects the transmission, because as the thickness increases, the rays bounce at the boundaries fewer times as they traverse the length of the waveguide.

Straight waveguide geometry in which the light traversing the structure encounters no bends or radii results in the greatest optical efficiency. However, due to ergonomic constraints or compatibility & management of essential accessories related to the device such as proximally attached fiber optic cables and suction tubing, it may be advantageous to design the proximal light input such that it creates an angle relative to the distal transmission body of the waveguide structure.

Referring now to FIGS. 6 and 6A, to preserve TIR and maximize transmission efficiency in illuminated waveguide 51 of suction apparatus 50, central portion 52 between light input section 54 and illuminated waveguide body 55 should be curved to form angle 53 between the input and body as close to 180 degrees as possible. Almost any bend or radius in the tube will cause some light leakage. However, if angle 53 in central portion 52 is limited to 150 degrees or greater, the light leakage is very low and the light transmission efficiency is maximized. Where angle 53 is less than 150 degrees, light leakage may be reduced by reducing or otherwise controlling the divergence of the light within the waveguide or by using any other suitable technique.

The shape of illuminated waveguide 51 morphs or cylindrically "sweeps" or "blends" from a solid cylindrical input, input section 54 into a circular hollow tube of waveguide body 55. Waveguide bore 56 may accommodate any suitable surgical tools such as suction tube 58. Suitable surgical tools access waveguide bore 56 through access opening 59. As discussed above, light exits waveguide body at or near distal end 60 with the majority of light exiting through distal surface 61. Distal surface 61 may be flat or it may any other suitable simple or complex shape. Distal surface 61 may have any of the surface features disclosed herein for extracting and directing light to a field of illumination.

Figure 16:
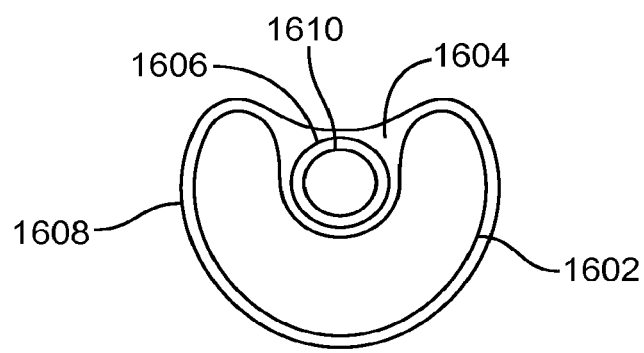
FIG. 16 illustrates an exemplary cross-section of an illuminated waveguide apparatus.

As the cross sectional area of illuminated waveguide 51 increases along the light transmission path from section 63 of input section 54 to central section 65, to distal cross-section 67 near distal end 60, the NA of the illumination waveguide increases, thus increasing the light divergence as light emerges from the distal end of the illuminator. The NA can also be influenced by bends. It may be possible to counter-bend to adjust the NA. Other techniques for controlling the NA of the waveguide may also include molding or machining features into the surfaces of the waveguide. The concepts illustrated above can also be manufactured as two halves that are over molded around any suitable surgical tool such as suction tube 58. FIGS. 6A-6C illustrate various cross-sections of the waveguide in FIG. 6, and FIG. 6D highlights the area surrounding opening 59. Thus, in the embodiment of FIG. 6B, a suction tube 1610 is disposed in the concave saddle portion 1604 of the waveguide 1602 as seen in FIG. 16. Optical cladding 1606 such as heat shrink tubing is disposed circumferentially entirely around the suction tube 1610, and then another layer of optical cladding 1608 such as heat shrink is dispose entirely around the circumference of both waveguide 1602 and suction tube 1610. A portion of the cladding on the suction tube contacts a portion of the outer cladding where no waveguide surrounds the suction tube. Additionally, in this embodiment, the inner saddle has a first radius of curvature and the outer surface has a different radius of curvature (here larger than the inner radius of curvature). Alternative embodiments may have other combinations of radii of curvature.

Figure 7:
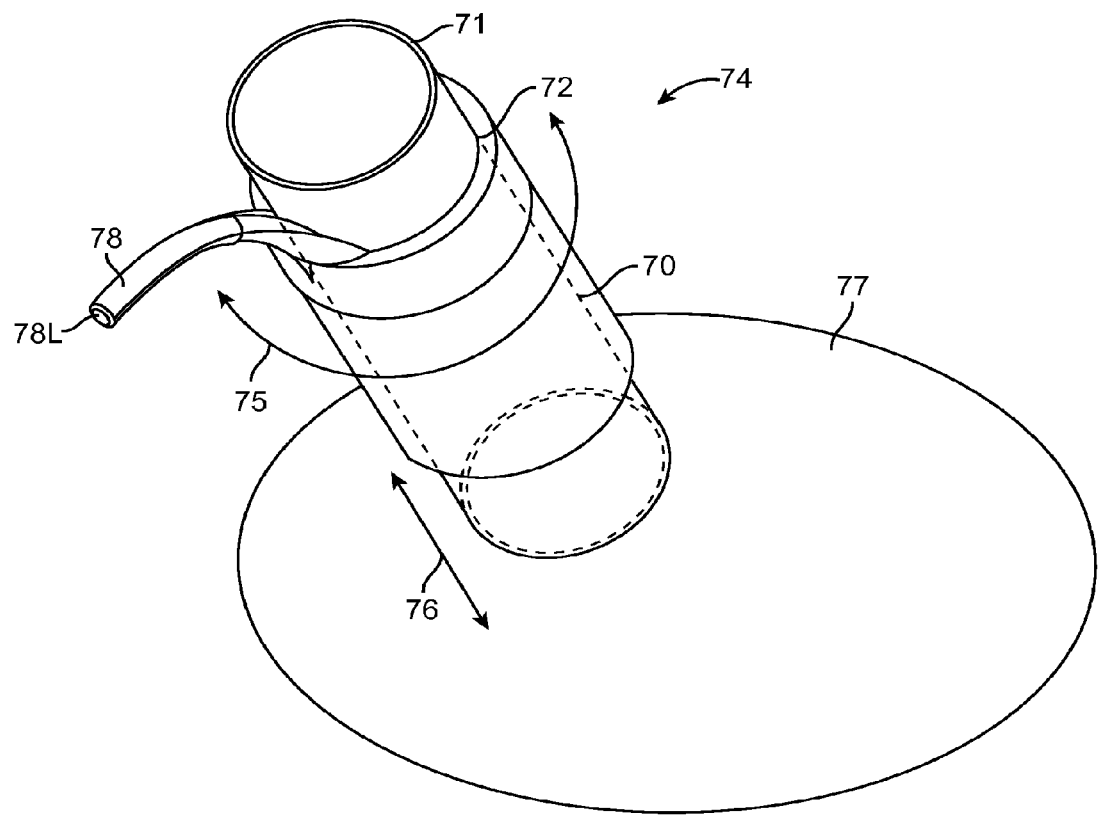
FIG. 7 is perspective view of the illumination input of an alternate illumination conduit.

Referring now to FIG. 7, disposable illuminated waveguide 70 can be supplied as a stand-alone device. Various suction devices or other suitable tools such as suction tool 71 can be inserted though central bore 72, the working channel of the illumination waveguide. A connection could be constructed between waveguide 70 and a surgical tool such as suction tool 71 that would allow the waveguide to be secured to various suction devices, enabling both waveguide 70 and suction tool 71 to be manipulated as a single unit. This concept can be applied to other devices that would fit through central bore 72 such as drills, etc. Additionally, illuminated surgical apparatus 74 lends itself to dynamic positioning of the waveguide 70 relative to any surgical tool inserted in central bore 72, such as suction tool 71. For example, the user could rotate the illuminator about the suction device as in rotation 75, as well as telescope illuminator along the length of the suction tube along path 76, repositioning or expanding or contracting illumination field 77 as needed during the procedure.

Figure 8:
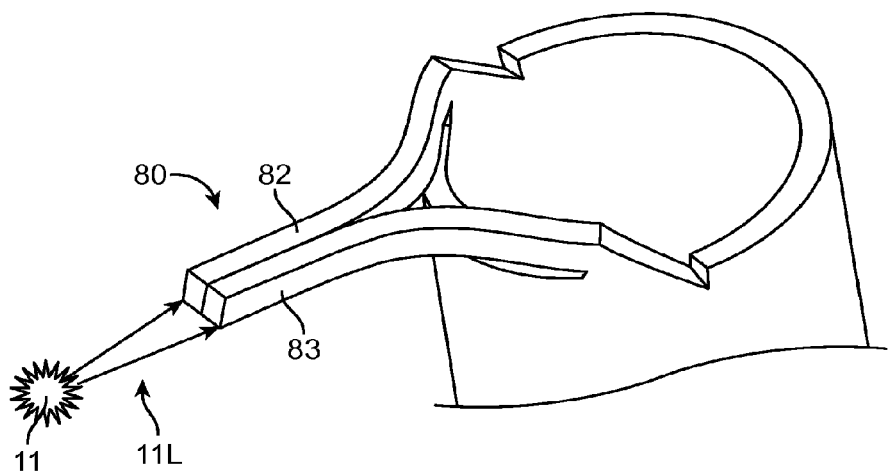
FIG. 8 is perspective view of the illumination input of another alternate illumination conduit.

An alternative approach involves splitting the solid input circle or ellipse such as input 78 of FIG. 7 and split input 80 is formed as in FIG. 8 in which half of input light 11L is directed to one half of the input, arm 82, and the other half of input light 11L is directed to the second half of the input, arm 83. Here, arms 82 and 83 come together in a generally rectangular cross-section as input 80 to engage fiber optic cable 11C. However, input 80 can have circular cross-section with semi-circular arm(s), elliptical or multi faceted for better mixing of light. Inputs 78 and 80 may be hollow or tubular and may also be shaped to operate as a lens or may include a plurality of lenses. The configuration could also have FEP cladding strategically applied to one or more areas of each arm to preserve TIR. To enable proper function of the light extraction features, holes, or other suitable shapes could be cut into the FEP or other cladding, enabling a desired balance of TIR preservation and suitable light leakage from specific zones of the device. In the embodiments of FIGS. 6, 6A-6D, and FIG. 7, a fiber optic cable may be coupled to the input portion of the waveguide thereby allowing light from an external light source to be delivered from the light source to the waveguide. The fiber optic cable may be releasably coupled with the light input portion of the waveguide, or the fiber optic cable may be a single piece fixedly coupled with the light input portion of the waveguide and integral therewith (e.g. by overmolding the fiber optic cable with the light input portion of the waveguide). The integrated fiber optic cable, or the releasably coupled fiber optic cable may be used with any of the waveguide embodiments disclosed herein. The integrated fiber optic cable or the releasable fiber optic cable may also be used in any of the other embodiments disclosed herein.

During fabrication, particularly injection molding, various artifacts may be formed in or on an optical part that may result in unpredictable performance of the optical part. Features such a gate scar, injector pin marks, parting lines, molded-in stress and any bends or sharp edges may create irregular and unpredictable output light patterns. To correct an irregular light output pattern the output surface of the waveguide may simply be roughened which will diffuse the light output. Roughened output surfaces cause significant efficiency loss and raise the output angle of the light. An alternative approach may be to create a pattern that projects multiple overlapping images of the defect pattern which will result in uniform illumination while minimizing efficiency loss and output angle. This can be achieved with a lens array on output surface such as lens array 24 of FIG. 2.

The design of a lens array for the input or output of an illumination waveguide should consider the focal length of the lenses, the quantity of lenses in the array, any suitable patterns for the array, and the spacing between the lenses. The lens focal length of the lenses needs to be selected to minimize diffusion, and to maximize the radius of the lenses of the array. The lens diameter should also consider the tooling to be used to create the lenses. Tool marks left or created by the tooling should be a small percentage of the diameter of the lenses. Similarly, making the lenses too small makes them difficult to manufacture and diffuses the light output. If the lenses are too large, there will be too few overlapping images and the resulting light pattern will not be uniform.

Incoherent and uncollimated light is going to diverge due to the geometry and refractive index of the waveguide; any divergence added by the lens array needs to be considered. Divergence of five to 10 degrees due to the lenses would be selected to maintain output light divergence close to the inherent divergence of the waveguide.

Lens array pattern is also important. The lens array pattern is a balance between manufacturing complexity and lens spacing. Hexagonal lenses provide minimal inter-lens spacing and minimal wasted space while maintaining light projection characteristics similar to spherical lenses. A rectangular lens array pattern may be selected of a square or rectangular spot pattern is desired. Similarly, a rectangular illumination pattern may be produced by varying the lens pitch between the X and Y dimensions in the plane of the output face on which the lenses are formed. For example, additional microstructure features can be added to the distal end of an illumination waveguide to optimize control of the illumination pattern as well as to homogenize the light output field. Anti-reflection features, typically diffractive in nature and sub-micron in size, can be added to the input and output faces of the illuminator to reduce normal Fresnel reflection losses. The features of the waveguide, such as curves, bends, and mounting features, can cause undesired reflections, light leakage, glare, and non-uniform output patterns resulting in poor performance. Adding microstructure features which may be refractive or diffractive on or near the distal portion of the illumination waveguide can potentially provide better light uniformity and or to bias the divergence or convergence of the illumination pattern as well to homogenize the light output of the illumination field. Features or tapering of the waveguide can also be added to the outside of an illumination waveguide to control the illumination output. Furthermore, micro lenses such as lens 78L or other micropattern structures can be added to an illumination waveguide input such as input 78 to better control the input beam shape or other light input characteristics. The light input arm can be round, square or multi faceted to provide a better mix of the light.

The waveguide can be made in various shapes or cross sections. Currently preferred cross-sectional shapes are round, elliptical, or hexagonal. Other cross-sectional shapes such as rectangles, triangles, or squares are possible. However, generally regular surfaces of the waveguide, as well as odd number of surfaces may cause a secondary pattern at the output. This pattern would manifest as bright and dark spots. Cross sections resembling even numbered higher order polygons such as the hexagon are currently preferred. As the number of faces in the cross-section increase, these cross sections would approach a circle, such a device design would potentially complicate manufacturing processing (such as injection molding), thereby increasing costs.

The illuminator can be tapered to increase or decrease its cross section as light travels from the input to extraction zones. Tapering biases the NA, causing either a tighter output spot (for increased area at the exit) or a larger more diffuse spot (decreased exit surface area, breaking TIR).

For an illuminated suction device, in many surgical applications, there is a need for circumferential illumination around the device. The illumination may need to be uniformly circumferential or delivered in an off axis orientation for most of the lighting to orient anterior to the retractor.

Figure 9:
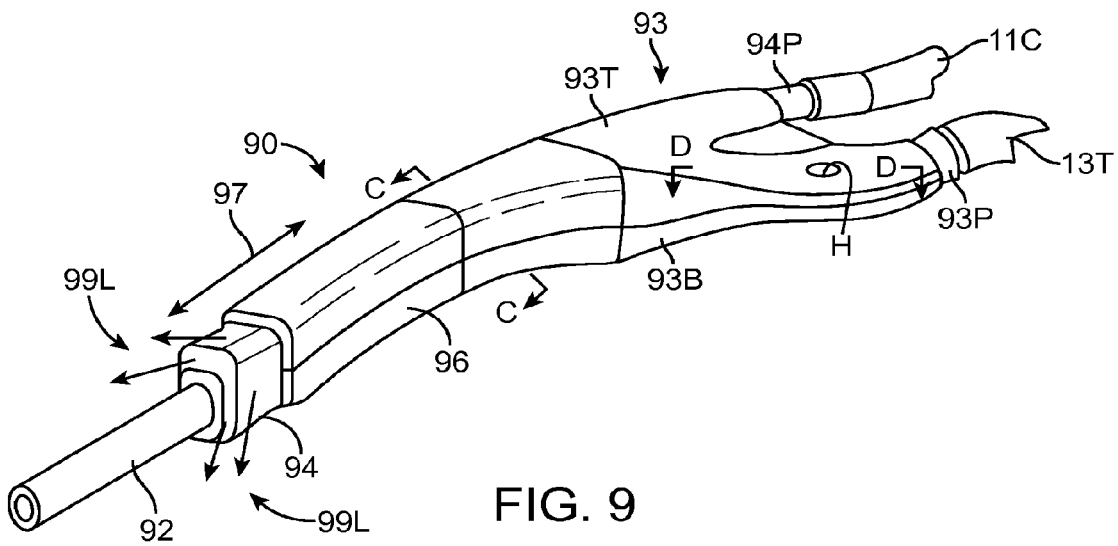
FIG. 9 is a perspective view of an illuminated suction apparatus with a handle.
Figure 10:
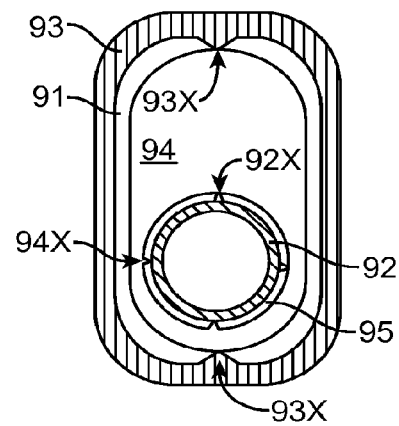
FIG. 10 is a cross section view of the illuminated suction apparatus of FIG. 8 taken along C-C.

Referring now to FIGS. 9 and 10, handle 93 of illuminated suction device 90 can be used to preserve TIR within illumination waveguide 94 through creation of air gap 91 (n=1.0) around waveguide 94. The design of the handle structure could include a portion that partially or fully covers the length of waveguide 94 to create the desired air gap. Features such as standoffs 93X can be molded into the surface of the handle in contact with the illuminator and need to be located in optical dead zones (zones where there is little or no TIR) to create a gap between components and minimize light leakage through the contact points. A similar configuration may be formed between suction tube 92 and illuminated waveguide 94, air gap 95 can be formed without standoffs based on the design tolerance between the ID of the illuminator and OD of the suction tube or with one or more standoffs such as standoff 92X or standoff 94X or any suitable combination. The air gaps between the handle/waveguide and/or waveguide/suction tube may be used in any of the illuminated suction apparatus embodiments disclosed herein.

The divergence of light output from illuminated waveguide 94 can be controlled by permitting all or a portion of distal casing 96 to slide along axis 97 over the illuminator. The user can slide the tube down over the illuminated waveguide 94 to reduce the divergence angle and reduce the divergence of light 99L.

Figure 11:
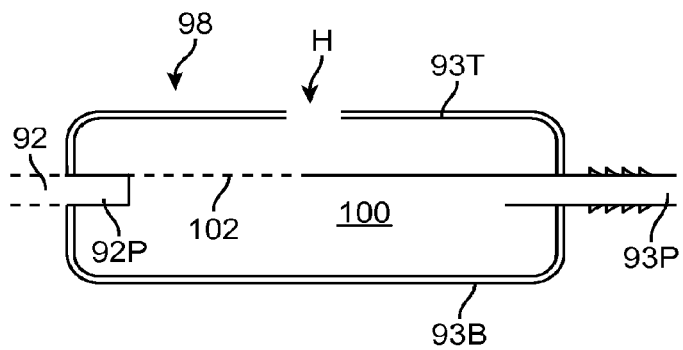
FIG. 11 is a cross section view of the handle of the illuminated suction apparatus of FIG. 10 taken along D-D.

Referring now to FIG. 11, the design of handle 93 must accommodate a suitable routing and termination of the suction channel and solid-state illuminator such that a suction flow control hole H is presented to the user in an ergonomically favorable position. Based on the way a user is expected to hold and manipulate an illuminated suction apparatus and the flow pattern of evacuated material from the patient, hole H may be present at or near the top surface 98 of the proximal handle. This can accomplished by forming handle 93 with at least two parts such as top section 93T and bottom section 93B. In addition to providing a shield for and proximal terminus for the illuminated waveguide 94, top handle portion 93T also contains suction flow control hole H. Suction flow control may also be provided by a valve or other similar apparatus that enables controlled adjustable suction. The top and bottom handle portions are sealed, with the bottom portion 93B creating a chamber in communication with proximal termination 92P of suction tube 92. Evacuated debris can be kept from flowing through to vacuum tube conduit 93P and out of hole H based on the geometry of the chamber 100 and pathway to flow control hole H. Alternatively a "strainer" or "filter" such as filter 102 may be included in handle 93 to capture any solid or liquid debris and prevent the debris from making their way out through hole H. Features in handle 93 could also allow the user to disassemble the top and bottom portions to clear any collected debris. The suction control mechanism may be used in any of the embodiments disclosed herein.

While the concepts presented thus far focus on a completely disposable non-modular device, alternative architectures are possible including the following:

a. Disposable suction tips (varying French sizes & styles such as yankaeur, etc.) that integrate with a disposable device through a "quick-connect" attach & detach scheme.

b. Disposable illumination sheaths such as waveguide sheath may accommodate any suitable surgical instrument such as for example, a drill, burr or endoscope which is encased, enclosed or otherwise surrounded by optical waveguide sheath. Illumination sheaths can be various materials such as flexible silicone.

c. Disposable distal suction tips or other implements (nerve probes, etc) can also be integrated with a reusable proximal illuminator containing a traditional fiber optic bundle. This would enable rapid tip style exchange without the need to unplug cables. This approach also provides a means of unclogging trapped evacuated material.

d. Reusable proximal handles with removable single use illuminators/suction tubes. Enables easy change-out of devices without need to unplug cables.

Figure 12:
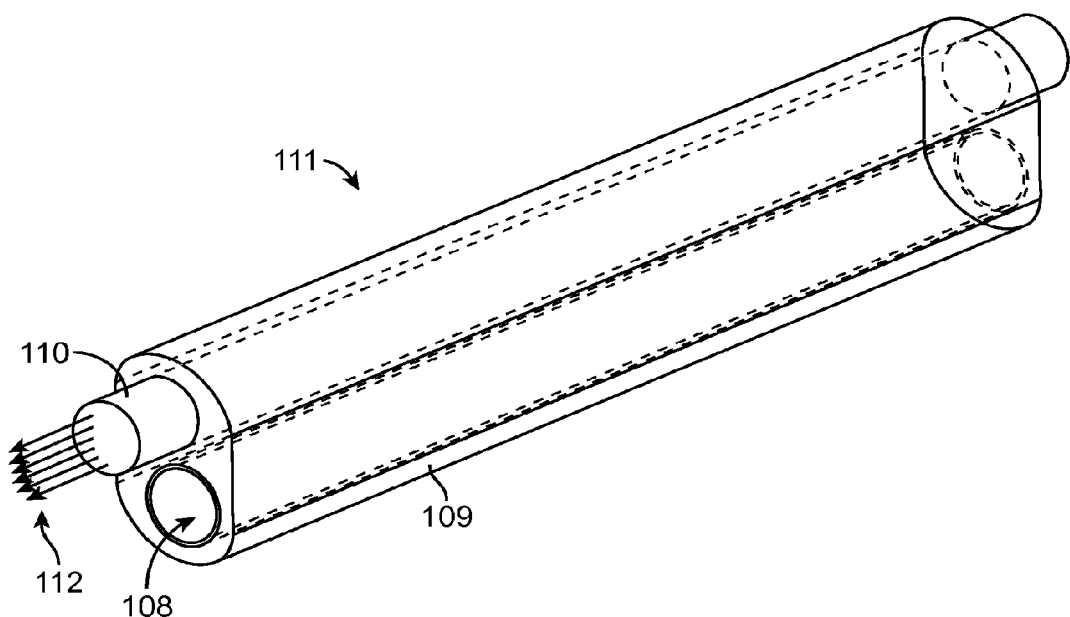
FIG. 12 is a perspective view of an alternate illuminated suction apparatus.

Referring now to FIG. 12, suction lumen 108 may be formed in suction element 109 that may be formed around an illuminator such as waveguide 110, as shown in illuminated suction apparatus 111. This configuration would allow for output light 112 to exit from a cylindrical source such as waveguide 110 without the shadowing caused by having a central illumination tube coaxial to the illuminator.

The routing of the suction conduit through the illuminator can be varied to optimize the illumination output and balance ergonomic considerations.

Figure 13:
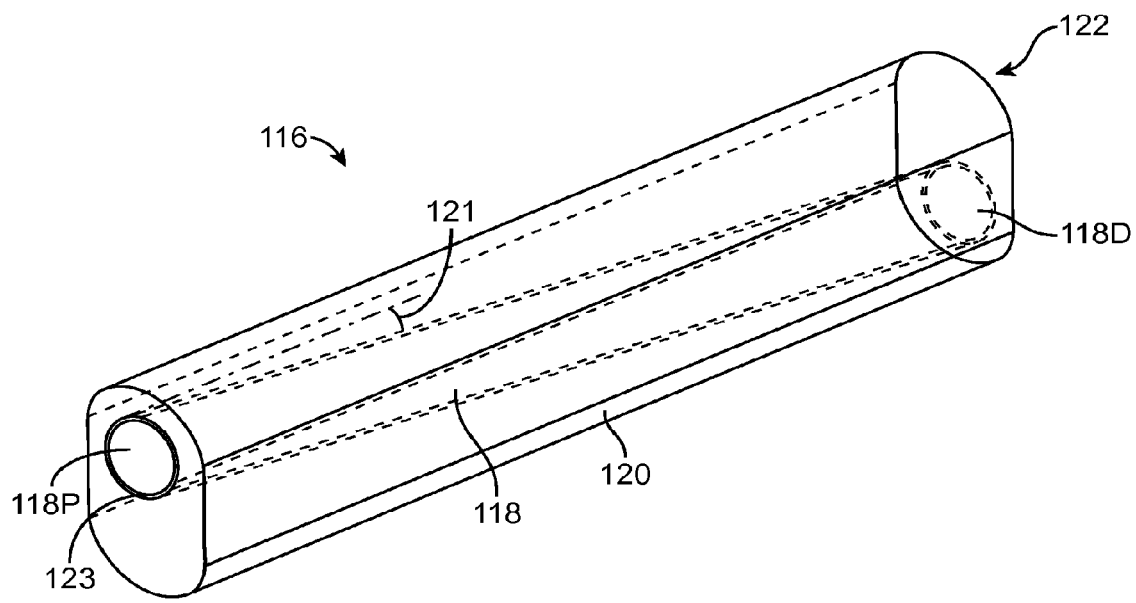
FIG. 13 is a perspective view of another alternate illuminated suction apparatus.

Referring now to FIG. 13, illuminated suction apparatus 116 is configured to enable suction tube 118 to be strategically routed through illumination waveguide 120 at angle 121 such that (1) proximal exposed end 118P is at the top of the device where the suction control function can be more readily accessed by the user; and (2) distal end 118D of the suction tube emerges from the bottom of the device below illumination output 122, providing optimized lighting of the surgical site from above the suction tube. In this configuration the suction tube changes light transmission paths through the illumination waveguide by introducing reflective surfaces which more thoroughly mix the light. It is possible to maintain the efficiency by using high reflective coatings, air gaps and cladding such as cladding 123. However, the added reflectance surfaces of the suction tube may cause the NA to increase.

Rotationally symmetric illuminated suction devices such as illuminated suction apparatus 116 may produce circumferential, uniform light output with strategic positioning of the suction tube that mitigates shadowing from the suction tube protruding from the distal surface of the waveguide. Light traversing the illuminated waveguide may have challenges with secondary reflectance surfaces, thus widening the light output pattern. Illuminated suction apparatus 116 is also expected to have a very large NA.

Illumination waveguides such as waveguides disclosed above may also be made malleable out of material like silicone. This can be useful to "pull over" an instrument like suction tube. The illumination waveguide can be made of a malleable material such as silicone allowing it to be pulled over a rigid suction tube, potentially lowering cost. Alternatively the malleable illumination waveguide material can be formed over a deformable suction tube structure, or a deformable structure that contains selective strength members (beams, etc). This would enable dynamic shaping of the suction tube to various desired shapes suited to the clinical application.

The illumination waveguide can be fabricated with materials of varying indices in a "stacked" or "composite" structure to shape and control the light output.

An alternative approach involves splitting an illumination waveguide with a solid light input with a circular or elliptical cross-section, routing and re-combining the waveguide into the original starting geometry. An illumination waveguide can then be molded over an internal suction tube. Alternatively, the suction tube in this configuration could run alongside the spit illuminator geometry.

If the cross section area is maintained (that is, distal and proximal ends on either side of split have same cross section, the intermediate shape of the waveguide can be manipulated. In the configuration listed above, there should be no significant loss of efficiency or change in NA. Thus, the input and output light patterns should be very similar in shape and intensity.

Figure 29:
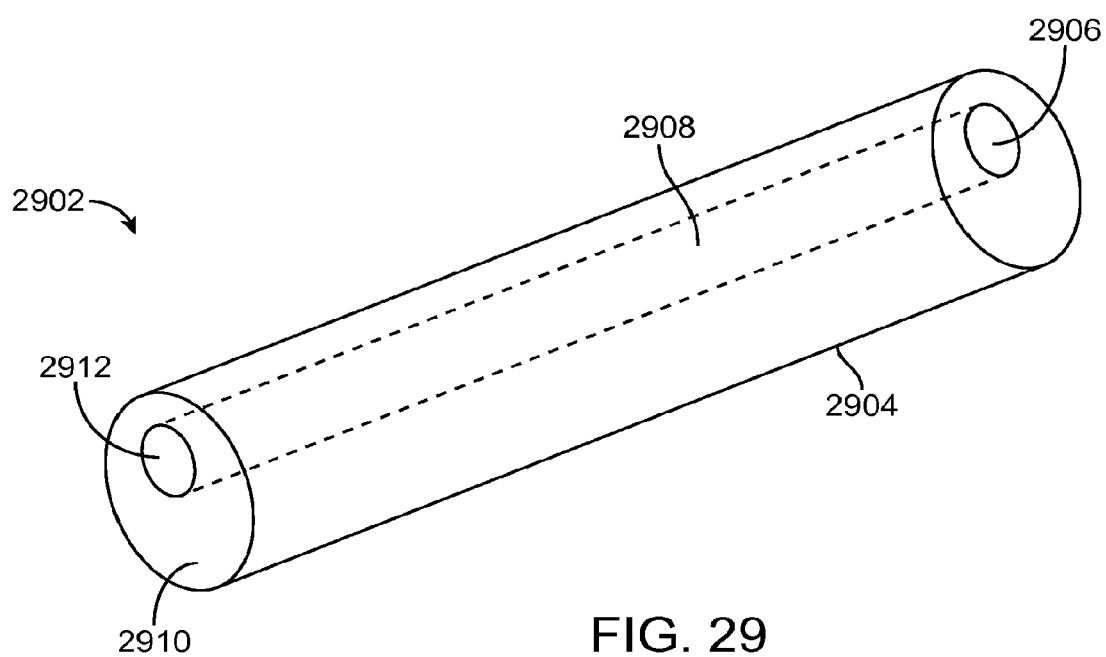
FIG. 29 illustrates an alternative embodiment of an illuminated suction apparatus.

FIG. 29 illustrates yet another embodiment of an illuminate suction apparatus 2902. The suction apparatus 2902 is a single molded piece 2904 that functions both as a suction tube and also as a waveguide. The molded piece 2904 is an elongate tubular structure having a lumen 2906 extending through the molded piece 2904. Thus, the molded piece 2904 may be used as a waveguide to transmit light distally by total internal reflection, and the lumen 2906 may be used as a suction tube to remove fluid and other debris from a surgical field. Light exiting the distal face 2910 illuminates the surgical field, and the distal end 2912 of the lumen is used to suction fluid and debris. The distal end 2912 of the lumen and the distal face 2910 may also be offset from one another and in preferred embodiments, the distal face 2910 is more proximal than the distal end 2912 of the lumen. Vacuum may be applied to the lumen 2906 using standard connectors and fittings, and light may be input into the waveguide using techniques known in the art. This embodiment has certain advantages such as allowing it to be molded as a single piece, and does not require a separate suction tube.

Figure 18B:
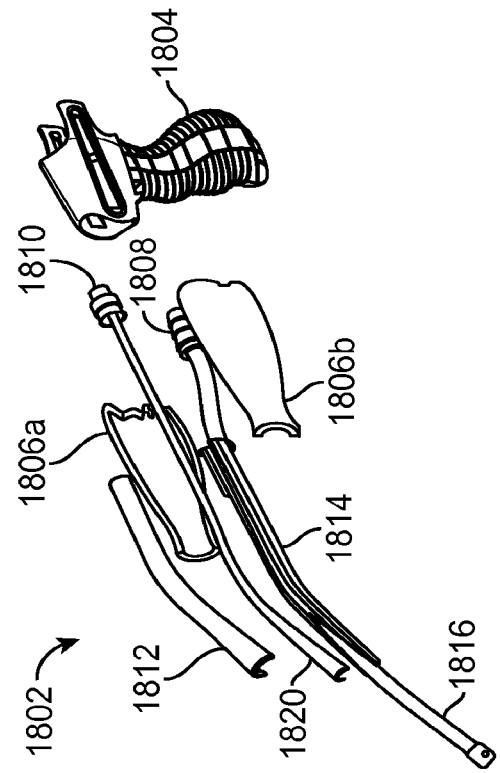
FIGS. 18A-18B illustrate another embodiment of an illuminated suction apparatus.
Figure 18A:
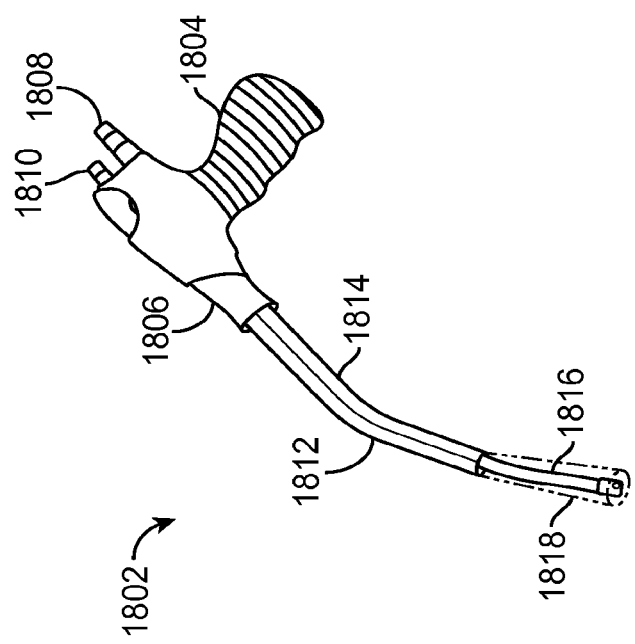

FIGS. 18A-18B illustrate another exemplary embodiment of an illuminated suction apparatus 1802. The apparatus 1802 includes an optional pistol grip handle 1804, a main handle 1806 formed from right and left handle sections 1806a, 1806b, a suction tube 1816, a non-fiber optic optical waveguide or illuminator 1820 (best seen in FIG. 18B) for emitting light 1818, an optical cladding 1812, optical connector 1810, and vacuum fitting 1808. FIG. 18B illustrates an exploded view of the illuminated suction apparatus 1802.

All or a portion of the suction tube tip may be modular such that a suction tip may be easily removed from the device and substituted with another suction tip depending on the anatomy being treated or the application (e.g. suction only, suction with electrical stimulation, etc.). Thus, various low profile tips may be provided with the illuminated suction device. The tips may be releasably coupled to the rest of the device using any number of quick release mechanisms such as bayonet fittings, threaded fittings, snap fits, detent mechanisms, etc.

Figure 19A:
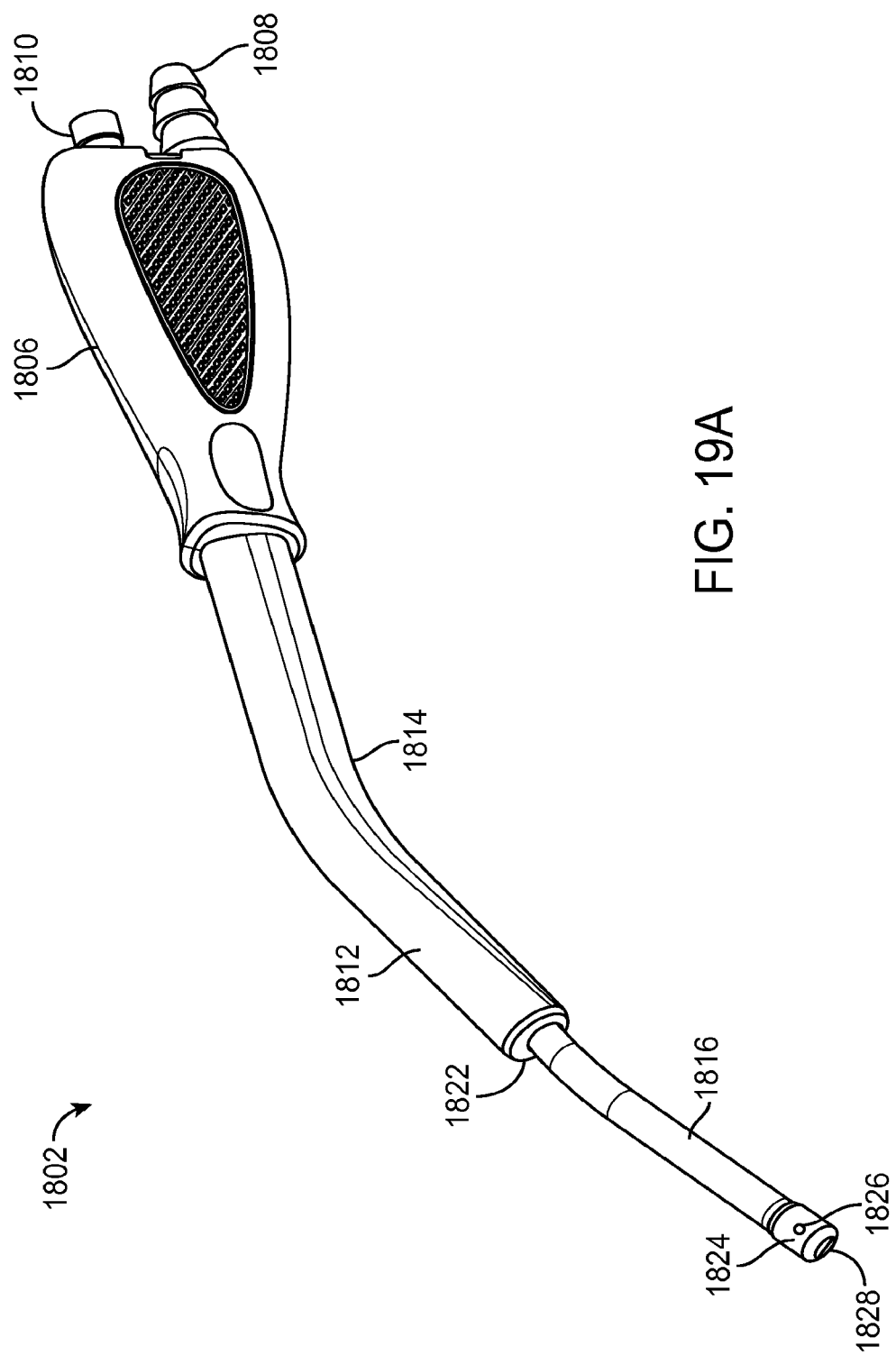
FIG. 19A illustrates a perspective view of the illuminated suction apparatus in FIGS. 18A-18B.

FIG. 19A illustrates a perspective view of the illuminated suction apparatus 1802 in FIGS. 18A-18B. The distal portion of the suction tube 1816 has an enlarged or bulbous head region 1824 to help prevent causing trauma with tissue during use. Additionally, suction holes 1826 may be disposed circumferentially around the outer surface of the suction tube 1816. The distal end of the suction tube may also have a suction hole 1828 for suctioning blood or other fluid and debris from the surgical field. The distal tip of the optical waveguide may include surface features 1822 for extracting and directing light to the surgical field. In this embodiment, the surface features form an array of lenses like those previously described above. Any of the surface features described herein may be used on the distal tip or on an outer surface of the distal region of the optical waveguide to extract and direct light to the surgical field. Some embodiments may have extraction features such as prisms, facets, lenses or other extraction features on an outer surface of the waveguide so that light is extracted from the outer surface of the waveguide and directed radially outward and circumferentially from the outer surface of the waveguide. The waveguide may be coated or clad with a layer of optical material to prevent light from leaking out. Exemplary cladding includes low index of refraction heatshrink materials. Air may also be used as is discussed below. FIG. 19A also illustrates the vacuum fitting 1808 which may be a standard barbed fitting, quick disconnect, or other fitting known in the art to allow the suction tube 1816 to be fluidly coupled to a vacuum source. The optical fitting 1810 may be any standard optical fitting such as an ACMI coupler to allow the optical waveguide to be optically coupled with an external light source. In other embodiments, the optical fitting 1810 may not be used, and the light source may include an LED or other source of light disposed in the handle 1806 or otherwise coupled to the illuminated suction apparatus 1802. In still other alternative embodiments, the source of light such as an LED may be disposed adjacent the distal tip of the optical waveguide.

Figure 19B:
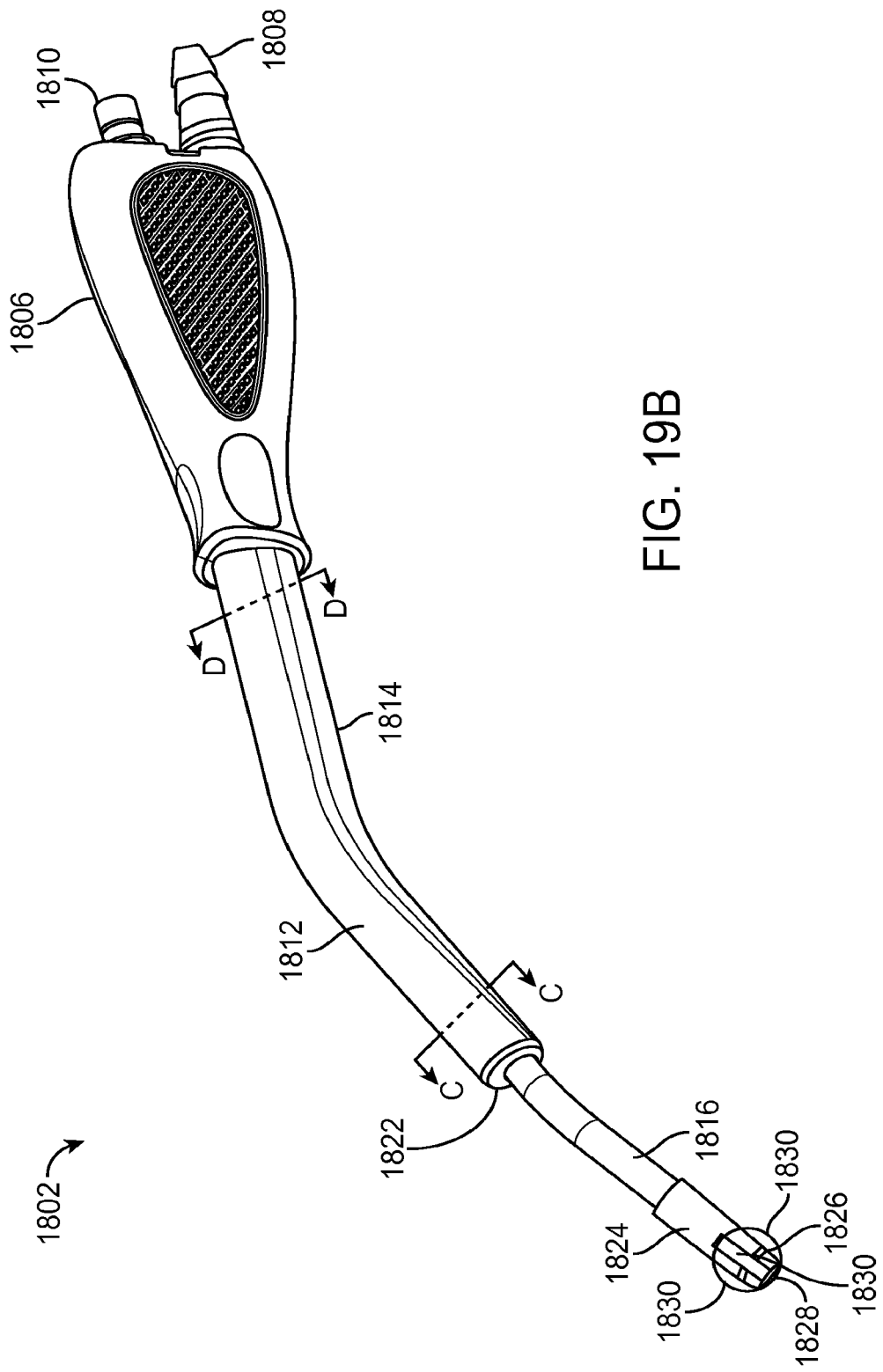
FIG. 19B illustrates an alternative embodiment of the illuminated suction apparatus in FIG. 19A.

FIG. 19B illustrates an alternative embodiment of an illuminated suction apparatus 1802 that is similar to the previous embodiment with the main difference being that the distal portion of the suction tube 1816 includes radially extending fins 1830 that form a whisk-like basket on the distal portion of the suction tube. The fins in the basket prevent tissue from being drawn into the suction holes 1826 causing blockage. The fins may be fixed to the suction tube or they may be radially expandable with adjustable size. In some embodiments, the fins may be conductive and some or all of the fins may also act as electrodes to electrically stimulate the tissue.

Figure 19C:
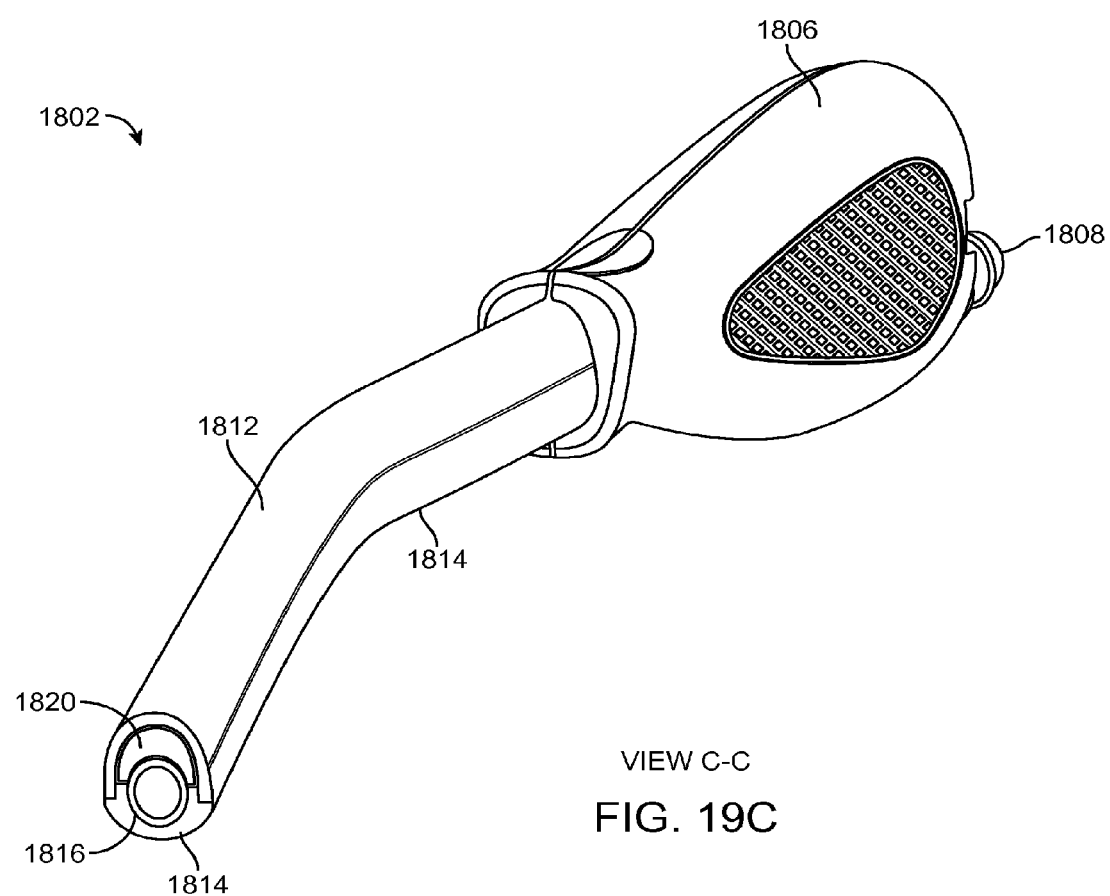
FIG. 19C illustrates a cross-section taken along the line C-C in FIG. 19B.

FIG. 19C illustrates a cross-section taken along the line C-C in FIG. 19B. It illustrates a distal portion of the illuminated suction apparatus proximal of the lenses and distal tip of the optical waveguide. The optical waveguide 1820 forms a C-shaped structure having a concave inner surface that is shaped to match the outer surface of the suction tube 1816, thus the concave region forms a saddle that receives the suction tube 1816 in order to minimize profile of the assembly. Additionally, the optical waveguide flares outward and is at least partially, or fully wrapped around the outer circumference of the suction tube, and thus light emitted from the optical waveguide will circumferentially illuminate an area around the suction tube. Thus the waveguide may have a cross-sectional area that changes, here increasing, while in other embodiments the cross-section may decrease, or it may remain constant. The cradle 1814 also has ledges which engage the optical waveguide to prevent or minimize direct contact between the optical waveguide and the suction tube. Preferably, an air gap is disposed therebetween. The air gap helps promote total internal reflection of the light passing through the optical waveguide. Contact between the optical waveguide and adjacent structures such as the suction tube result in light loss which reduces transmission efficiency of the optical waveguide. Additionally, the outer shield or cladding 1812 similarly engages ledges on the cradle to minimize or prevent direct contact between the outer cladding and the optical waveguide by forming an air gap therebetween. In some embodiments, it may be desirable to provide a barrier that prevents blood or other fluid from wicking up the suction device along the air gap. The barrier may be an O-ring, adhesive, or any other material disposed between the waveguide and suction tube, or anywhere else where there is a gap for fluid to flow through such as between the waveguide and the outer shield. The barrier may be placed anywhere along the device such as at the distal tip, or more proximally to prevent the fluid from wicking. The outer cladding is preferably a molded elongate cap element that is placed over the optical waveguide to prevent blood or other fluid and debris from contacting the optical waveguide. It is preferably formed from a polymer having a low index of refraction. The closer to an index of 1 (the index of refraction for air), the better. In some embodiments, the cap may directly contact the optical waveguide and light loss is minimized due to the refractive index of the cap. In still other embodiments, instead of the cap, only a layer of air cladding is disposed over an outer surface of the waveguide.

Figure 19D:
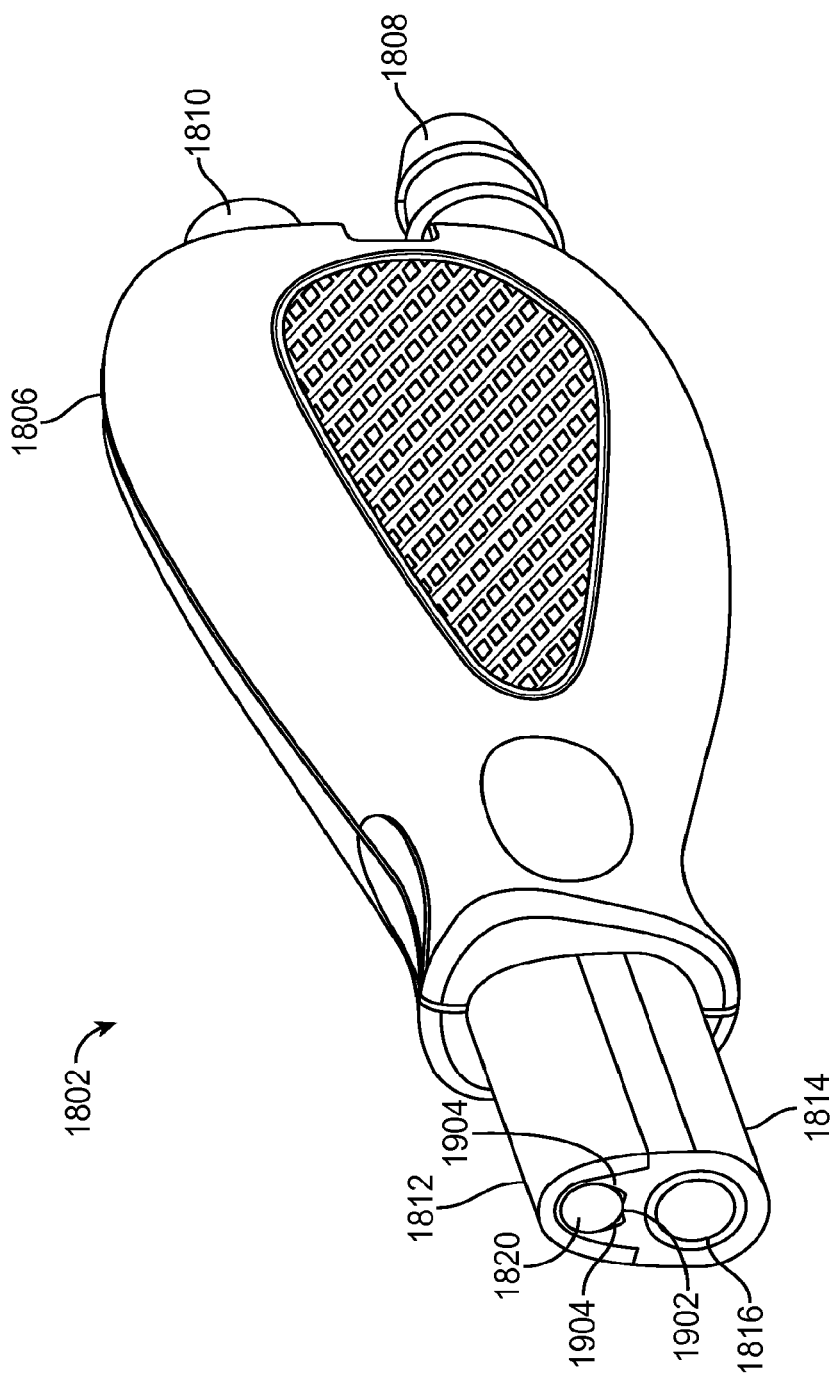
FIG. 19D illustrates a cross-section taken along the line D-D in FIG. 19B.

FIG. 19D illustrates a cross-section of the illuminated suction apparatus 1802 taken along the line D-D in FIG. 19B. It illustrates a portion of the illuminated suction apparatus that is more proximal than in FIG. 19C, and closer to the handle 1806. It shows that the optical waveguide 1820 is cylindrical. Thus, it is clear that the optical waveguide has a cross-section which changes from the proximal end toward the distal end. In this embodiment, it changes from the round cylindrical region to wider the C-shaped distal region. Also, it is clear that thickness decreases distally along the optical waveguide. FIG. 19D also illustrates the cradle 1814 with a channel 1902 having corners that engage the optical waveguide 1820 at point contacts 1904 or with minimum contact area.

Figure 20A:
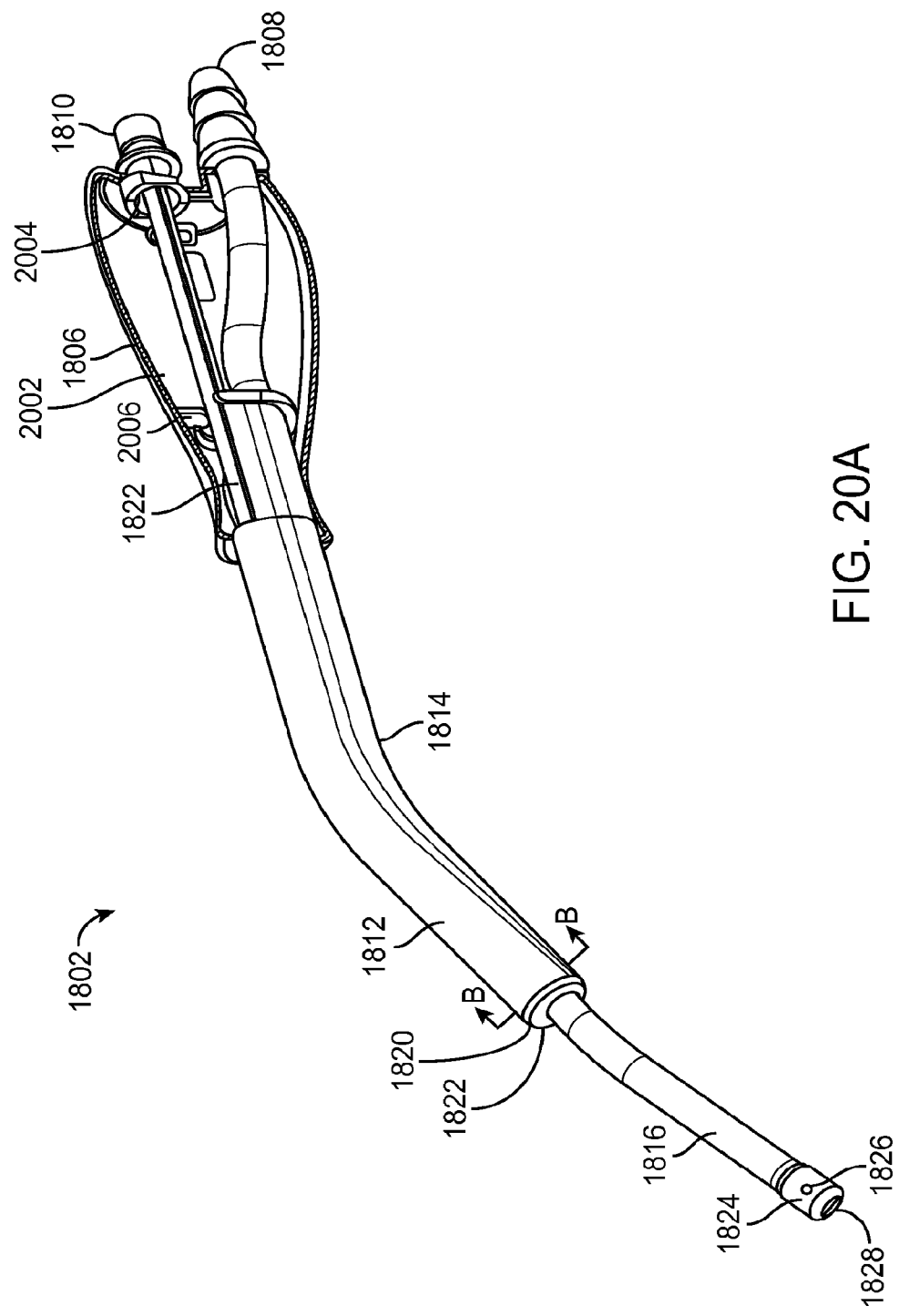
FIGS. 20A-20C illustrate various partial cross-sections of the embodiment in FIG. 19B.
Figure 20B:
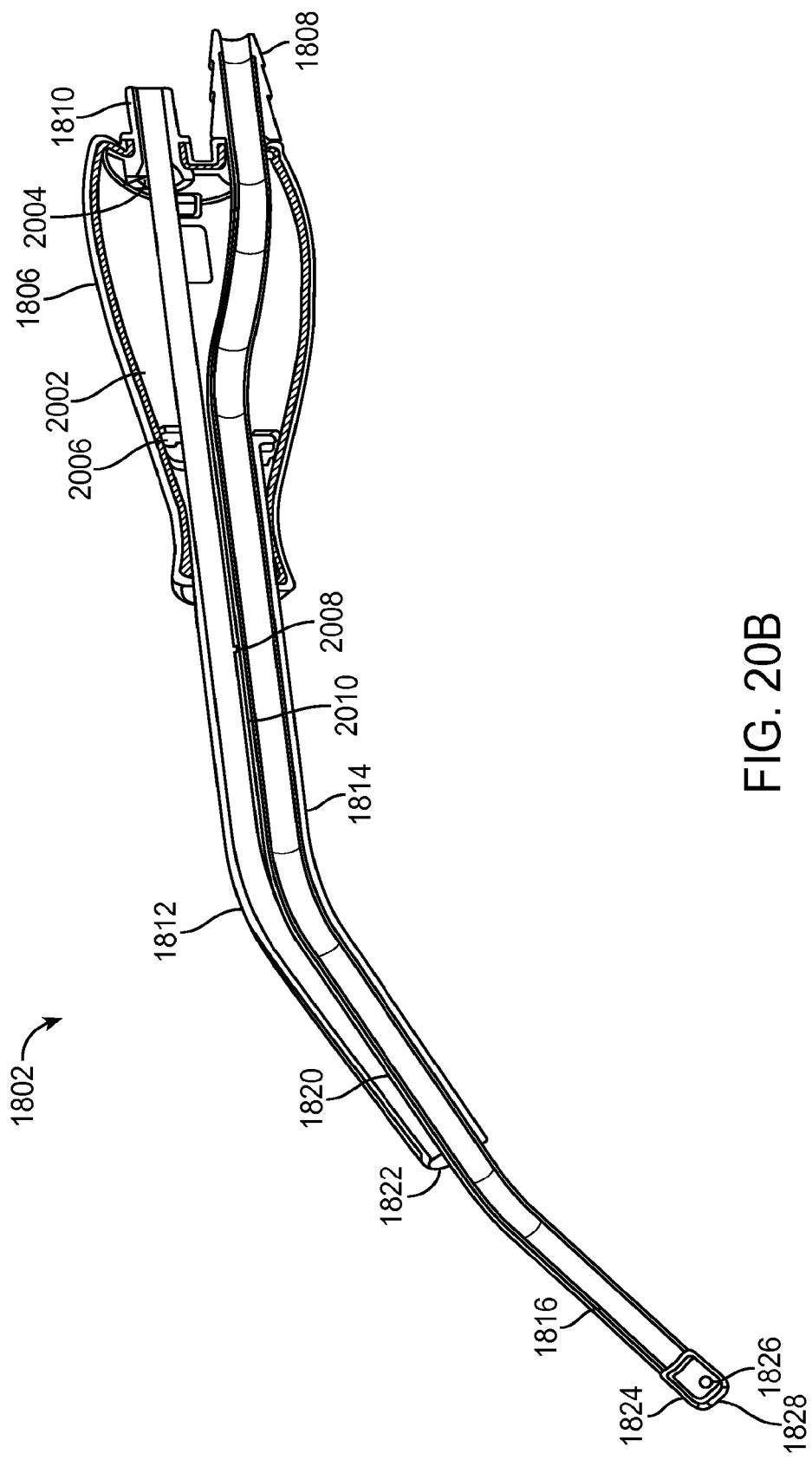
Figure 20C:
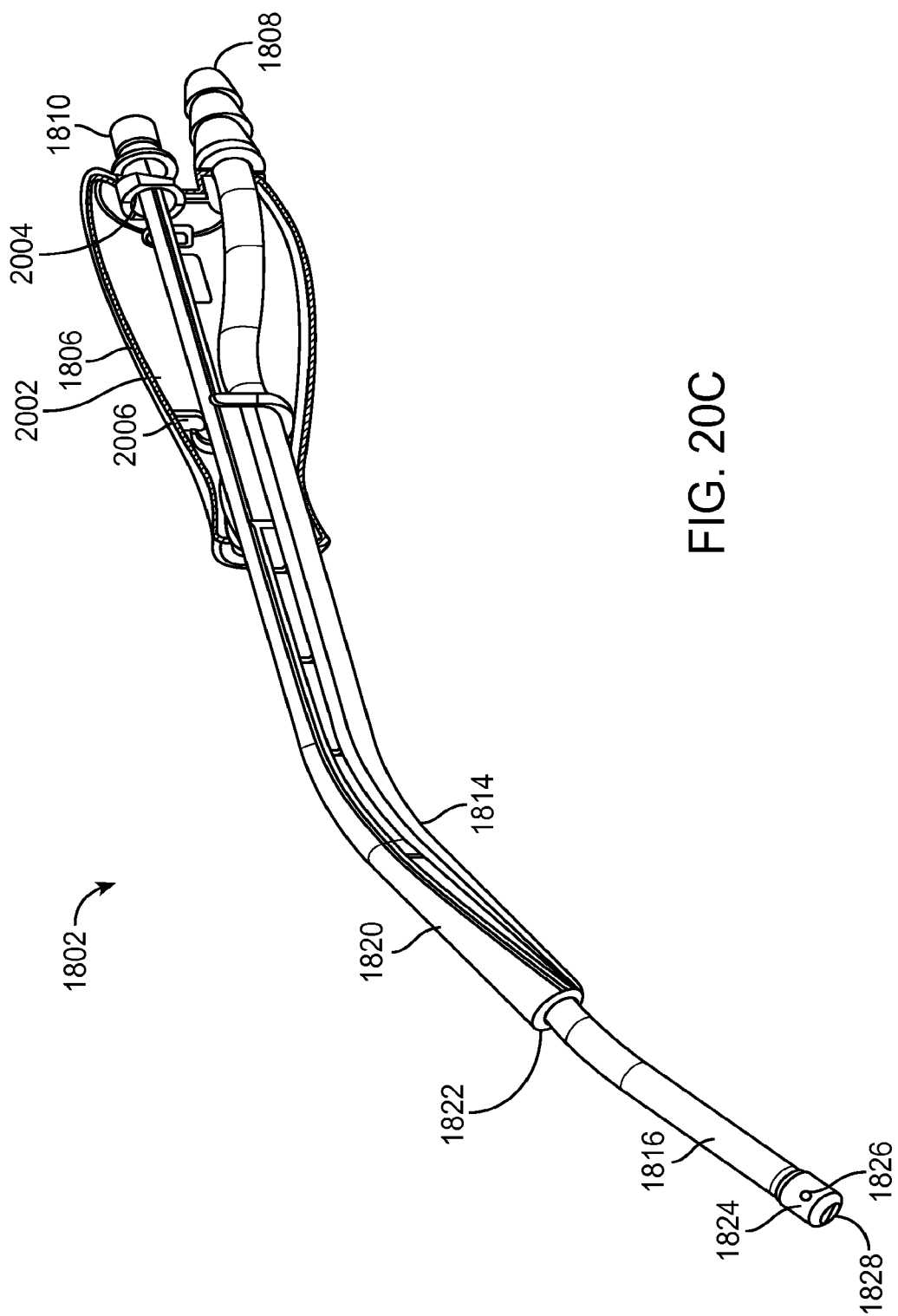

FIGS. 20A-20C illustrate various partial cross-sections of the illuminated suction apparatus 1802 in FIG. 19B. In FIG. 20A, a portion of the handle 1806 has been removed to illustrate the air gap 2002 that surrounds the optical waveguide 1822 in the handle region, as well as the air gap 2004 that is circumferentially disposed around the optical waveguide as it enters the optical fitting 1810, here an ACMI adapter. Standoffs 2006 formed from ribs in the handle have minimum contact with the optical waveguide and help provide support to the optical waveguide so that the air gap may be maintained. FIG. 20B illustrates a partial cross-section taken along the line B-B in FIG. 20A and more clearly illustrates the air gaps 2002, 2004 surrounding the optical waveguide 1820. Additionally, ribs 2008 in the cradle 1814 also form standoffs that help maintain an air gap 2010 between the optical waveguide 1820 and the suction tube 1816. FIG. 20C illustrates a partial cross-section of the illuminated suction apparatus 1802 with the cladding layer 1812 removed.

Figure 21:
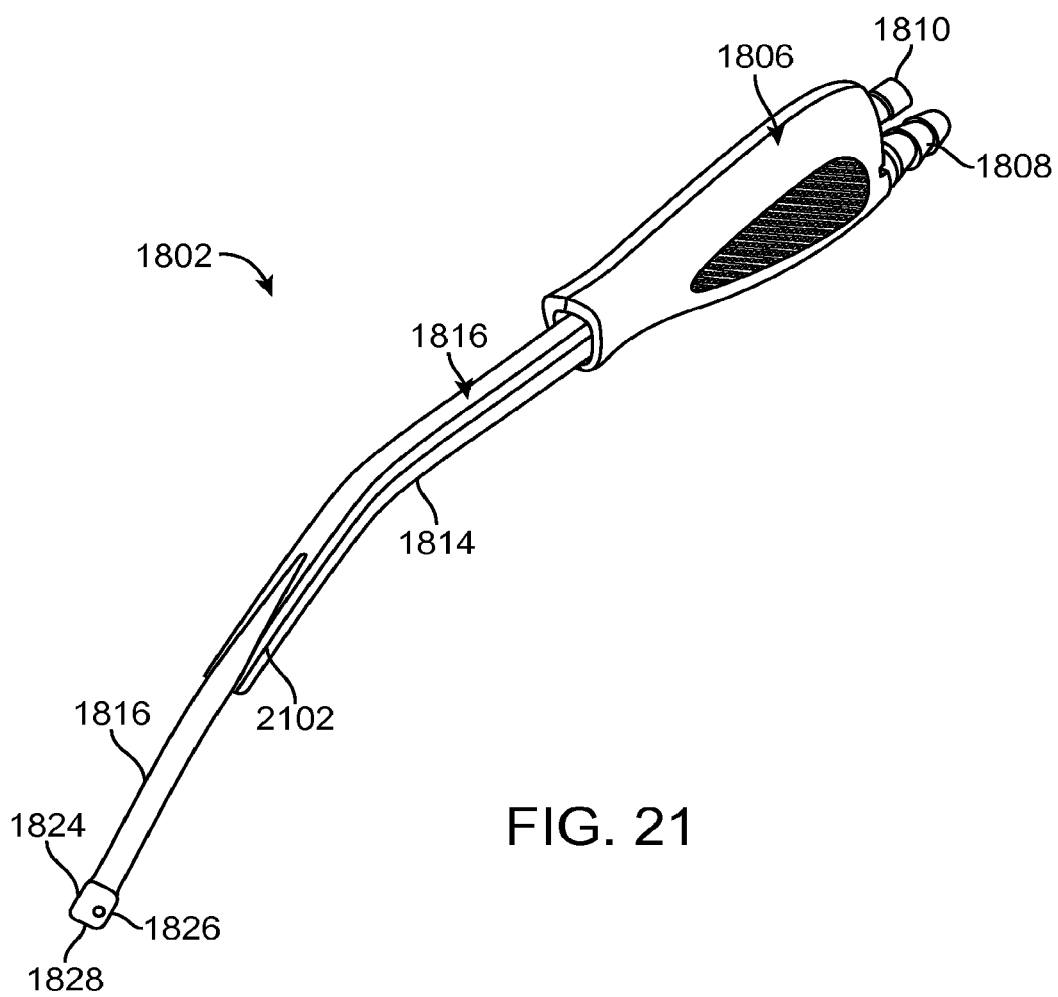
FIG. 21 illustrates a perspective view of the embodiment in FIG. 19B with the cladding and optical waveguide removed.

FIG. 21 illustrates a perspective view of the embodiment in FIG. 19B with the cladding and the optical waveguide removed. This view highlights the cradle 1814 which completely surrounds a proximal portion of the suction tube 1816 and only partially surrounds the suction tube toward the distal end thereof. Additionally, a ledge or shelf 2102 forms standoffs that support the optical waveguide, thereby helping to provide an air gap that surrounds the optical waveguide.

Figure 22:
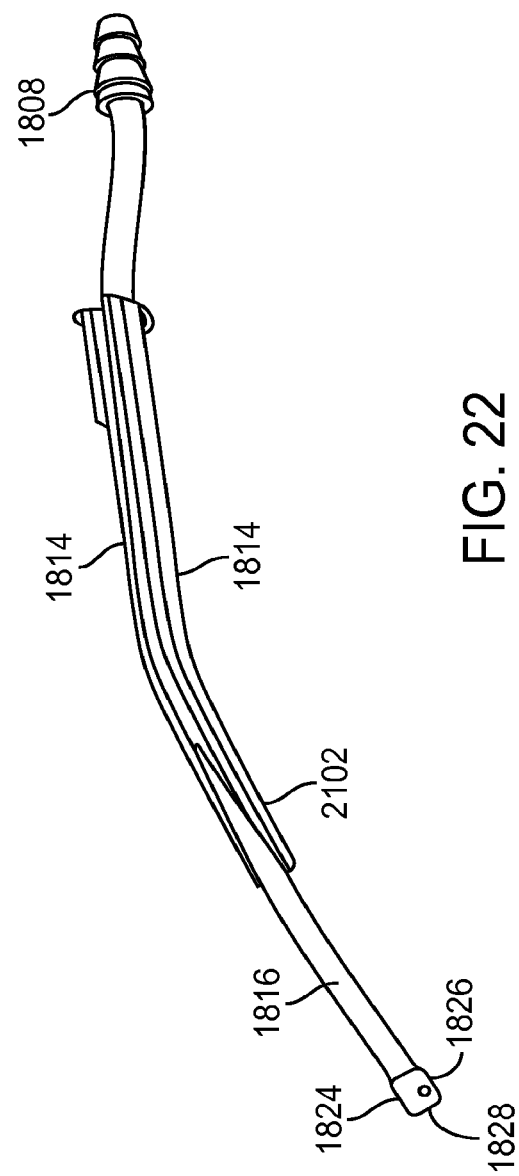
FIG. 22 illustrates the suction tube and cradle of the embodiment in FIG. 19B.
Figure 23:
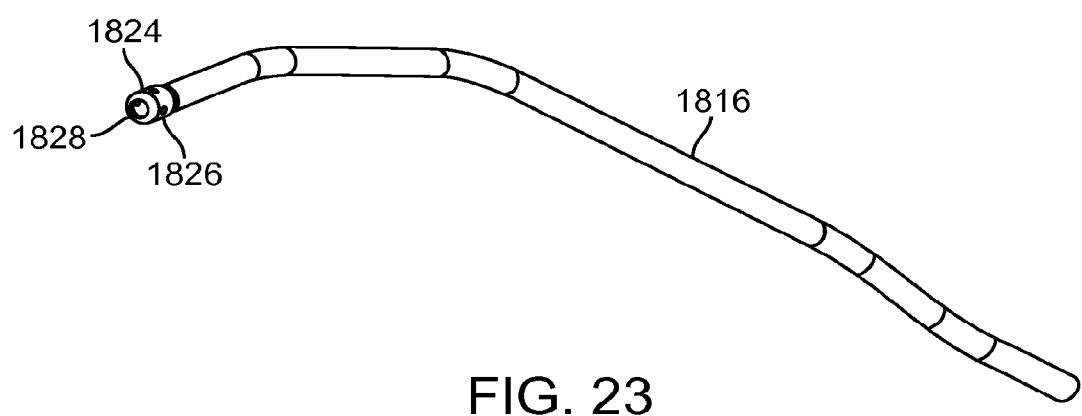
FIG. 23 illustrates the suction tube of the embodiment in FIG. 19B.
Figure 24:
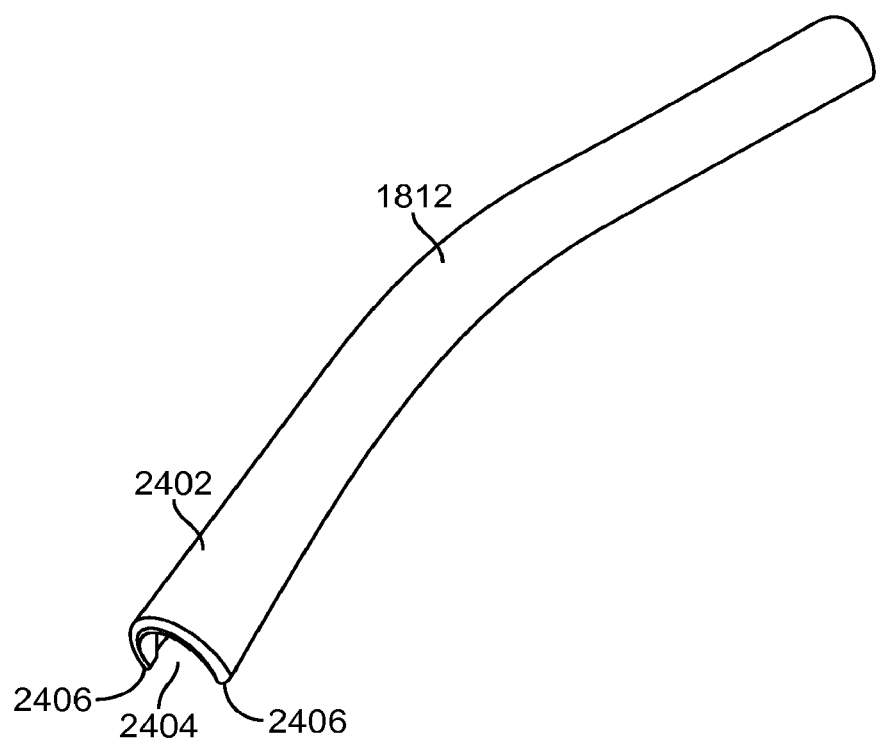
FIG. 24 illustrates the cladding of the embodiment in FIG. 19B.

FIG. 22 illustrates the suction tube 1816 disposed in the cradle 1814 of the embodiment in FIG. 19B. It more clearly illustrates the ledge 2102 which supports the optical waveguide. FIG. 23 illustrates the suction tube 1816. It has a bent distal portion that is shaped so that the handle may fit comfortably in the operator's hand while allowing the tip to be easily inserted into the surgical field. Any shaped may be used on the suction tube depending on the anatomy being treated. The present embodiment and shape may be used in general surgery procedures, as well as other procedures. In still other embodiments, the suction tube may be formed from a malleable material so that the operator may bent the suction tube to any desired shaped. In still other embodiments, the suction tube may be conductive and act as an electrode to deliver current to tissue in the surgical field. In still other embodiments, electrodes may be coupled to the suction tube. Any of the electrode configurations described below may be used in this embodiment. Additionally, the suction tube may be coated or covered with a layer of insulation to prevent current from flowing out of unwanted areas of the suction tube. FIG. 24 illustrates the cladding 1812. As previously described, it preferably is an injection molded elongate polymer element having an outer surface 2402 that is formed into a C-shaped component so that edges 2406 may be placed into engagement with the standoffs on the cradle to minimize contact therebetween. Additionally, the concave region 2404 may be sized and shaped to match and receive the optical waveguide while maintaining an air gap therebetween if desired, or the cladding may directly engage the optical waveguide. Preferred embodiments are formed from a material having a low index of refraction in order to prevent or minimize light loss between the cladding and the optical waveguide where the two components contact one another.

Figure 25:
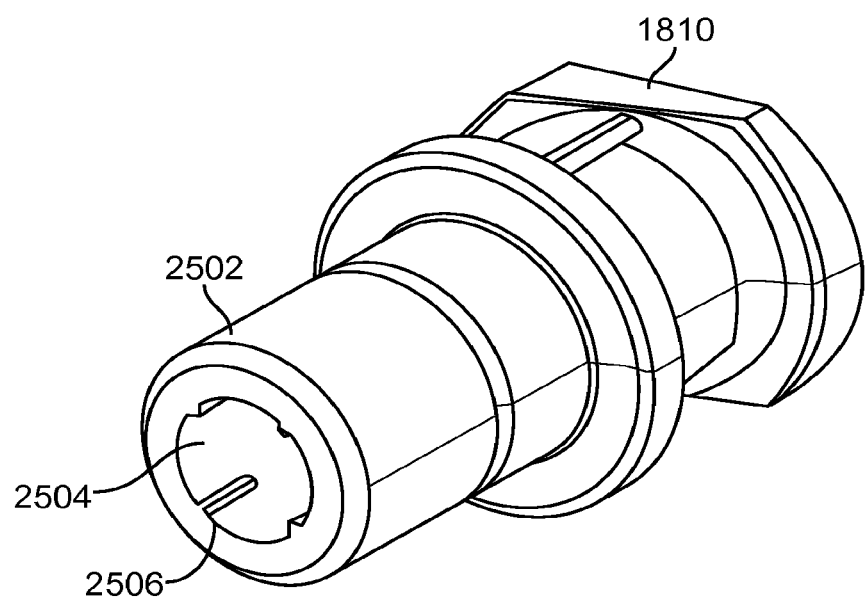
FIG. 25 illustrates an exemplary optical coupling.

FIG. 25 illustrates an exemplary optical coupling 1810 that may be used with any of the illuminated suction embodiment described herein. It preferably is compliant with other ACMI optical couplings. The outer surface 2502 may be optically coupled with an external light source. The internal channel 2504 is sized to receive the optical waveguide. Ribs 2506 may be disposed in the internal channel to minimize contact between connector and the waveguide thereby allowing an air gap to be formed around the optical waveguide which helps to minimize light loss.

Figure 26A:
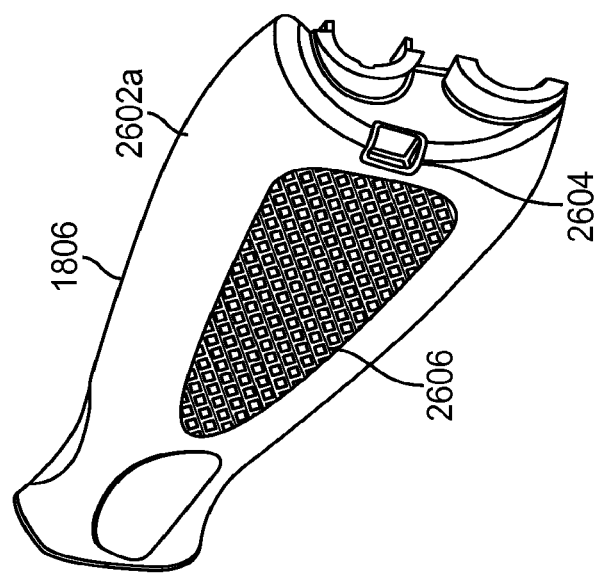
FIGS. 26A-26B illustrate an exemplary handle.
Figure 26B:
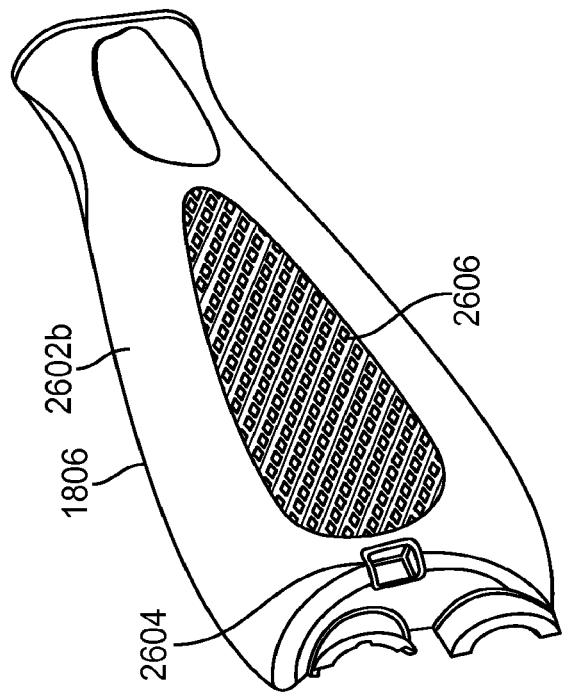
Figure 27:
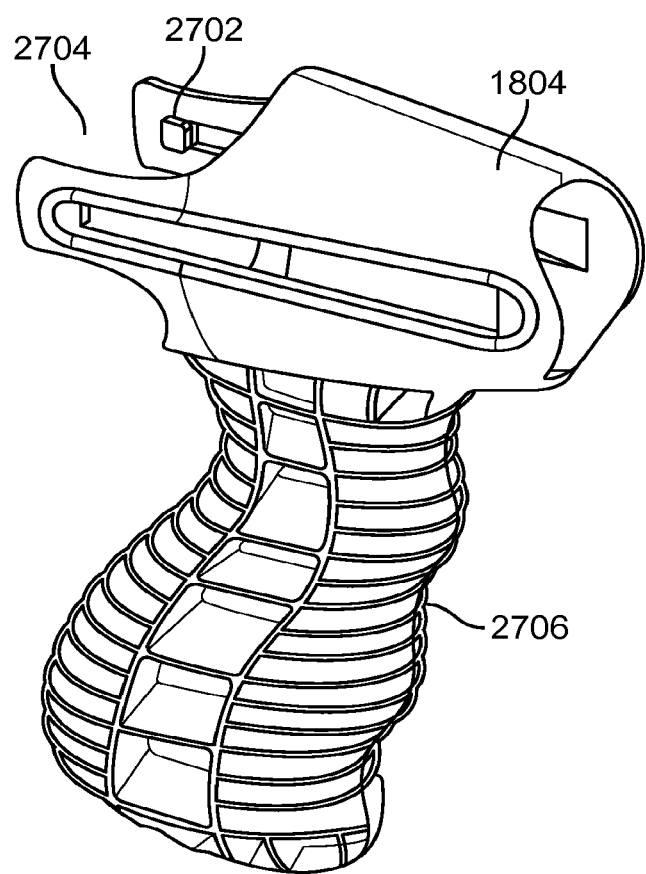
FIG. 27 illustrates an exemplary pistol grip handle.

FIGS. 26A-26B illustrate the right 2602a and left 2602b halves of the handle 1806. The outer surface may be textured so that the operator can easily grasp the handle. Additionally, the handle 1806 may have an engagement mechanism 2604 such as snap fittings or other mechanism for releasably or fixedly coupling the optional pistol grip handle with the main handle. FIG. 27 illustrates the optional pistol grip handle 1804 which has a central channel 2704 for receiving the main handle 1806. Cooperating snaps or other engagement mechanisms 2702 may be disposed on the pistol grip for releasably or fixedly engaging the main handle with the pistol grip handle. The pistol grip handle may have texturing or other surface features 2706 to facilitate grasping by the operator.

Figure 28A:
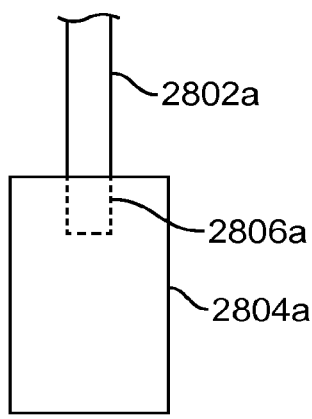
FIGS. 28A-28D illustrate various light inputs to the waveguide.
Figure 28B:
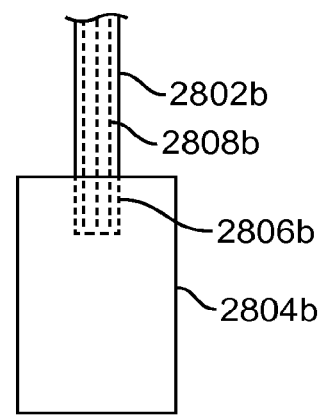

In any of the embodiments described herein, the light input may be coupled to a proximal portion of the optical waveguide using a number of techniques. For example, in FIG. 28A, the light input may be a single light pipe 2802a which is received in a receptacle 2806a in the waveguide 2804a. The light pipe 2802a may then be bonded in position using an index matching optical adhesive. In other embodiments, the waveguide may be overmolded around the light pipe, thereby forming a single integral piece. In FIG. 28B, the light input 2802b may be a bundle of optical fibers 2808b which are received in the receptacle 2806b of waveguide 2804b. The fibers may be bonded as described previously, or the overmolding processing may be used. This light input may be referred to as a pigtail.

Figure 28C:
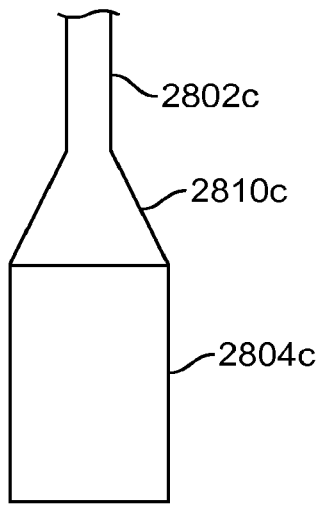
Figure 28D:
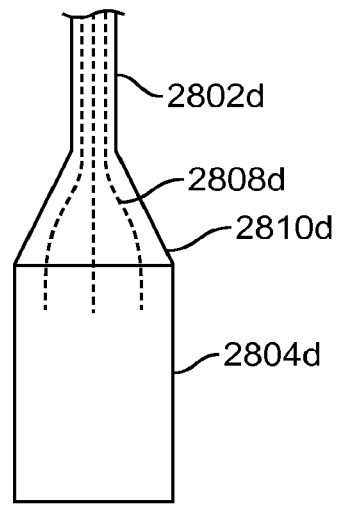

FIG. 28C illustrates a single optical light pipe 2802c which flares outward 2810c to match the width of the optical waveguide 2804c. This helps spread the light along the width of the waveguide, thereby more evenly distributing the light. FIG. 28D illustrates a similar embodiment that uses a bundle of fibers 2808d in the input 2802d instead of a single light pipe. The fibers flare out 2810d to match the width of the optical waveguide 2804d. In any of these embodiments, bonding, overmolding, or other techniques known in the art may be used to couple the light input to the waveguide.

Figure 31A:
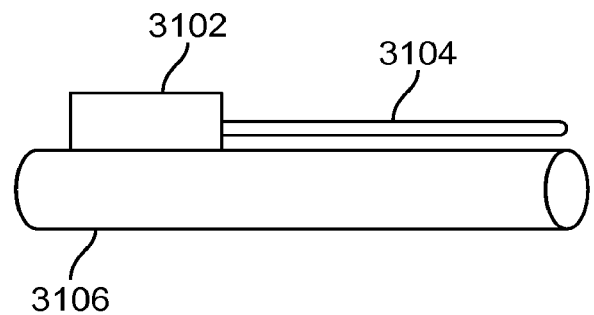
FIGS. 31A-31B illustrate an exemplary embodiment of an illuminated and malleable suction device.
Figure 31B:
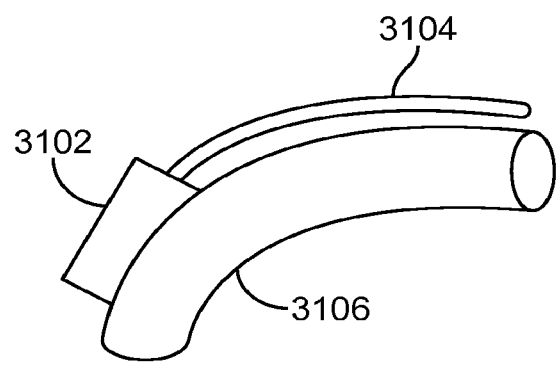

FIGS. 31A-31B illustrate still another exemplary embodiment of a malleable and illuminated suction device. The suction device may have a suction tube 3106 that generally takes the same form as any of the previously described suction tubes. However, in this embodiment, the suction tube 3106 is malleable and thus it may be bent in any direction in order to direct the suction to a desired position in the surgical field. Additionally, if the suction tube acts as an electrode or has electrodes disposed on it, bending the suction tube also helps to direct electrical current to a desired position in the surgical field. A waveguide 3102 that may take the form of any of the previously described waveguides may be coupled with the suction tube. A flexible light input 3104 maybe coupled with the waveguide. The flexible input 3104 may take the form of any of the previously described light inputs, including the pigtail described above. In FIG. 31A, the suction tube 3106 is in a substantially linear configuration. In FIG. 31B, the distal portion of the suction tube has been deflected downward to form a curved tip. The waveguide bends with the suction tube, and similarly, the light input also flexes with the suction tube. Thus, the suction tube may be bent in any direction without requiring the re-adjustment of the waveguide or light input cable. In some embodiments, portions of the suction tube may be rigid to prevent them from being bent, while other portions may be bendable. For example, the distal portion may be bendable, while the proximal portion may remain rigid. Preferably, the bendable portions maintain their bent positions until manipulated into another position.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, any of the features disclosed in one embodiment of an illuminated suction apparatus may be used in any of the other embodiments of illuminated suction apparatuses disclosed herein. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A hand-held illuminated suction device comprising:
   a suction tube having a proximal portion and a distal portion;
   an optical waveguide having a proximal region and a distal region, wherein light is transmitted from the proximal region toward the distal region thereof by total internal reflection;
   a first handle coupled to the proximal portion of the suction tube and also coupled to the proximal region of the optical waveguide, wherein the first handle is disposed around the proximal region of the optical waveguide; and
   at least one total internal reflection (TIR) preserving feature coupled to the optical waveguide, wherein the at least one TIR preserving feature is configured to promote total internal reflection of the light passing through the optical waveguide.

2. The device of claim 1, wherein the first handle is disposed around the proximal region of the optical waveguide, and wherein the at least one TIR preserving feature comprises an air gap disposed between the first handle and the proximal region of the optical waveguide.

3. The device of claim 2, wherein the at least one TIR preserving feature further comprises one or more standoffs disposed between the proximal region of the optical waveguide and an interior wall of the first handle, the one or more standoffs maintaining the air gap disposed between the first handle and the proximal region of the optical waveguide.

4. The device of claim 1, wherein the first handle is ergonomically configured to fit in an operator's hand.

5. The device of claim 1, further comprising a pistol grip handle coupled to the first handle.

6. The device of claim 1, wherein the proximal portion of the suction tube is configured to be fluidly coupled to a vacuum source, and wherein the distal portion is configured to remove fluid or debris from a surgical field.

7. The device of claim 1, wherein the suction tube comprises an outer surface and the optical waveguide is disposed over the outer surface of the suction tube.

8. The device of claim 1, wherein the distal region of the optical waveguide comprises a plurality of light extraction features configured to direct the light distally to illuminate a surgical field.

9. The device of claim 1, wherein the at least one TIR preserving feature comprises an optical' cladding disposed over an outer surface of the optical wave guide.

10. The device of claim 9, wherein the optical cladding is further configured to prevent or minimize contact between the optical waveguide and fluid, debris, or tissue in a surgical field.

11. The device of claim 9, wherein the first handle is disposed over at least a portion of the optical cladding.

12. The device of claim 9, wherein the optical cladding comprises a TIR promoting coating.

13. The device of claim 9, wherein the at least one TIR preserving feature comprises an air gap between the optical cladding and the optical waveguide, and wherein the optical cladding is configured to maintain the air gap.

14. The device of claim 1, wherein the at least one TIR preserving feature comprises an air gap between a portion of the suction tube and a portion of the optical waveguide, wherein the at least one TIR preserving feature further comprises one or more standoffs disposed between the optical waveguide and the suction tube, and wherein the one or more standoffs prevent engagement between the portion of the suction tube with the portion of the optical waveguide thereby maintaining the air gap.

15. A method of illuminating tissue in a surgical field of a subject, said method comprising:
   providing an illuminated suction apparatus having a suction tube, an optical waveguide, a first handle coupled to the suction tube and optical waveguide, and at least one total internal reflection (TIR) preserving feature coupled to the optical waveguide, wherein the suction tube, optical waveguide, first handle, and the at least one TIR preserving feature are coupled together to form a single handheld instrument;
   promoting total internal reflection of light passing through the optical waveguide with the at least one TIR preserving feature;
   advancing a distal region of the illuminated suction apparatus into the surgical field;

illuminating the surgical field with light from the optical waveguide; and suctioning debris or fluid from the surgical field with the suction tube while illuminating the surgical field.

16. The method of claim 15, wherein the at least one TIR preserving feature comprises a first air gap between a proximal region of the optical waveguide and the first handle, and wherein promoting total internal reflection of the light passing through the optical waveguide comprises maintaining the first air gap.

17. The method of claim 16, wherein the at least one TIR preserving feature comprises one or more standoffs disposed between a proximal region of the optical waveguide and an interior wall of the first handle, and wherein maintaining the first air gap comprises providing the one or more standoffs.

18. The method of claim 16, wherein the at least one TIR preserving feature comprises a second air gap between the suction tube and the optical waveguide, and wherein promoting total internal reflection of the light passing through the optical waveguide comprises maintaining the second air gap.

19. The method of claim 18, wherein the at least one TIR preserving feature comprises one or more standoffs disposed between the suction tube and the optical waveguide, and wherein maintaining the second air gap comprises providing the one or more standoffs.

20. The method of claim 19, wherein providing the cladding further comprises preventing the fluid and debris in the surgical field from contacting the optical waveguide with the optical cladding.

21. The method of claim 20, wherein at least one TIR preserving feature further comprises an air gap between the optical cladding and the optical waveguide, and wherein the optical cladding is configured to maintain the air gap.

22. The method of claim 21, wherein at least one TIR preserving feature further comprises one or more standoffs disposed between the optical waveguide and the suction tube, and wherein the one or more standoffs prevent engagement between a portion of the suction tube with a portion of the optical waveguide thereby maintaining the air gap therebetween.

23. The method of claim 19, wherein the optical cladding comprises a coating promoting the total internal reflection of the light passing through the optical waveguide.

24. The method of claim 15, wherein the at least one TIR preserving feature comprises an optical cladding disposed over the optical waveguide, and wherein promoting total internal reflection of light passing through the optical waveguide comprises providing the cladding.

25. The method of claim 15, wherein the first handle is ergonomically configured to fit in an operator's hand.

26. The method of claim 15, wherein the illuminated suction apparatus further comprises a pistol grip handle coupled to the first handle.

* * * * *